US012723242B2

(12) United States Patent
Kwon et al.

(10) Patent No.: US 12,723,242 B2
(45) Date of Patent: Sep. 1, 2026

(54) GLUTAMINE-HYDROLYZING GMP SYNTHASE VARIANT AND METHOD FOR PRODUCING PURINE NUCLEOTIDE BY USING SAME

(71) Applicant: CJ CHEILJEDANG CORPORATION, Seoul (KR)

(72) Inventors: Nara Kwon, Seoul (KR); Ji Hyun Lee, Seoul (KR); Hyun-jung Bae, Seoul (KR); Dae Young Kim, Seoul (KR); Eun Ji Kim, Seoul (KR); Lan Huh, Seoul (KR); Hyeryun Yoo, Seoul (KR); Bina Kim, Seoul (KR); Sung Kwang Son, Seoul (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 33 days.

(21) Appl. No.: 17/911,876

(22) PCT Filed: Dec. 17, 2021

(86) PCT No.: PCT/KR2021/019303

§ 371 (c)(1),
(2) Date: Sep. 15, 2022

(87) PCT Pub. No.: WO2023/048343

PCT Pub. Date: Mar. 30, 2023

(65) Prior Publication Data

US 2024/0209342 A1 Jun. 27, 2024

(30) Foreign Application Priority Data

Sep. 23, 2021 (KR) ........................ 10-2021-0125841

(51) Int. Cl.
*C12N 9/00* (2006.01)
*C12P 19/32* (2006.01)

(52) U.S. Cl.
CPC ................ *C12N 9/93* (2013.01); *C12P 19/32* (2013.01); *C12Y 603/05002* (2013.01)

(58) Field of Classification Search
CPC .... C12N 9/93; C12P 19/32; C12Y 603/05002
See application file for complete search history.

(56) References Cited

U.S. PATENT DOCUMENTS

2013/0095529 A1 4/2013 Cho et al.
2020/0347346 A1 11/2020 Kim et al.

FOREIGN PATENT DOCUMENTS

EP 3 722 430 A1 10/2020
JP 2000-300272 A 10/2000
KR 10-0655902 B1 12/2006
KR 10-2010-0127784 A 12/2010
KR 10-2011-0016417 A 2/2011
KR 10-2019-0090657 A 8/2019

OTHER PUBLICATIONS

Q58970, NCBI GenPept, version Q58970.1 annotation updated Aug. 12, 2020, obtained from < https://www.ncbi.nlm.nih.gov/protein/ 44887896?sat=48&satkey=124177657 > on Apr. 17, 2025 (Year: 2020).*

GUAAA_METJA, Q58970, version Q58970.1 annotation updated Aug. 12, 2020, NCBI GenPept, obtained from < https://www.ncbi.nlm.nih.gov/protein/ 44887896?sat=48&satkey=124177657 > (Year: 2020).*

Singh et al., Curr. Protein Pept. Sci. 18:1-11, 2017 (Year: 2017).*

Zhang et al., Structure 26:1474-1485, 2018 (Year: 2018).*

Franco et al., "Biochemical characterization of recombinant guaA-encoded guanosine monophosphate synthetase (EC 6.3.5.2) from *Mycobacterium tuberculosis* H37Rv strain," *Archives of Biochemistry and Physics* 517:1-11 (2012).

NCBI Reference Sequence: WP_006823296.1, "glutamine-hydrolyzing GMP synthase [Corynebacterium casei]," 2 pages (Dec. 9, 2019).

NCBI Reference Sequence: WP_040355890.1, "glutamine-hydrolyzing GMP synthase [Corynebacterium ammoniagenes]," 2 pages, (Dec. 9, 2020).

NCBI Reference Sequence: WP_194285183.1, "glutamine-hydrolyzing GMP synthase [Corynebacterium stationis]," 1 page (Nov. 16, 2020).

Tesmer et al., "The crystal structure of GMP synthetase reveals a novel catalytic triad and is a structural paradigm for two enzyme families," *Nature Structural Biology* 3(1):74-86 (1996).

* cited by examiner

*Primary Examiner* — David Steadman
*Assistant Examiner* — Scott E. Mulder
(74) *Attorney, Agent, or Firm* — Seed Intellectual Property Law Group LLP

(57) ABSTRACT

The present application relates to a glutamine-hydrolyzing GMP synthase variant and a method for producing a purine nucleotide by using the same.

11 Claims, No Drawings

Specification includes a Sequence Listing.

SEQUENCE LISTING

<160> NUMBER OF SEQ ID NOS: 51

<210> SEQ ID NO 1
<211> LENGTH: 530
<212> TYPE: PRT
<213> ORGANISM: Artificial sequence
<220> FEATURE:
<223> OTHER INFORMATION: Synthetic seqeunce guaA_R29C

<400> SEQUENCE: 1

Met Thr Gln Pro Ala Thr Thr Pro Arg Pro Val Leu Val Val Asp Phe
1 5 10 15

Gly Ala Gln Tyr Ala Gln Leu Ile Ala Arg Arg Val Cys Glu Ala Ser
20 25 30

Ile Tyr Ser Glu Val Val Pro His Ser Ala Thr Val Lys Glu Ile Lys
35 40 45

Ala Lys Asn Pro Ala Ala Leu Ile Leu Ser Gly Gly Pro Ser Ser Val
50 55 60

Tyr Ala Asp Gly Ala Pro Gln Leu Lys Pro Glu Leu Leu Glu Leu Gly
65 70 75 80

Val Pro Val Phe Gly Ile Cys Tyr Gly Phe Gln Ala Met Asn His Ala
85 90 95

Leu Ala Leu Gly Gly Asn Val Ala Gln Thr Gly Asp Arg Glu Tyr Gly
100 105 110

Arg Thr Glu Ile Thr His Thr Gly Gly Val Leu His Asp Gly Leu Glu
115 120 125

Glu Asn His Lys Val Trp Met Ser His Gly Asp Ala Val Asp Lys Ala
130 135 140

Pro Glu Gly Phe Thr Val Thr Ala Ser Ser Ala Gly Ala Pro Val Ala
145 150 155 160

Ala Met Glu Cys Val Ala Lys Gln Met Ala Gly Val Gln Tyr His Pro
165 170 175

Glu Val Met His Ser Pro His Gly Gln Glu Val Leu Val Arg Phe Leu
180 185 190

Thr Glu Val Ala Gly Leu Glu Gln Thr Trp Thr Ser Ala Asn Ile Ala
195 200 205

Gln Gln Leu Ile Asp Asp Val Arg Ala Gln Ile Gly Pro Glu Gly Arg
210 215 220

Ala Ile Cys Gly Leu Ser Gly Gly Val Asp Ser Ala Val Ala Ala Ala
225 230 235 240

Leu Val Gln Arg Ala Ile Gly Asp Arg Leu Thr Cys Val Phe Val Asp
245 250 255

```
His Gly Leu Leu Arg Ala Gly Glu Arg Glu Gln Val Glu Lys Asp Phe
            260                 265                 270

Val Ala Leu Ala Ser Thr Gly Ala Lys Leu Ile Thr Ala His Glu Ala
        275                 280                 285

Asp Ala Phe Leu Ser Lys Leu Ala Gly Val Thr Asp Pro Glu Ala Lys
    290                 295                 300

Arg Lys Ala Ile Gly Ala Glu Phe Ile Arg Ser Phe Glu Arg Ala Val
305                 310                 315                 320

Ala Gln Ala Leu Glu Glu Ser Pro Glu Asp Ser Thr Val Asp Phe Leu
                325                 330                 335

Val Gln Gly Thr Leu Tyr Pro Asp Val Val Glu Ser Gly Gly Gly Asp
            340                 345                 350

Gly Thr Ala Asn Ile Lys Ser His His Asn Val Gly Gly Leu Pro Asp
        355                 360                 365

Asp Val Glu Phe Glu Leu Val Glu Pro Leu Arg Leu Leu Phe Lys Asp
    370                 375                 380

Glu Val Arg Ala Leu Ala Val Gly Arg Glu Leu Gly Leu Pro Glu Glu
385                 390                 395                 400

Ile Val Ala Arg Gln Pro Phe Pro Gly Pro Gly Leu Gly Ile Arg Ile
                405                 410                 415

Ile Gly Glu Val Thr Glu Glu Arg Leu Glu Ile Leu Arg Gln Ala Asp
            420                 425                 430

Leu Ile Ala Arg Thr Glu Leu Thr Asn Ala Gly Leu Asp Gly Asp Ile
        435                 440                 445

Trp Gln Cys Pro Val Val Leu Leu Ala Asp Val Arg Ser Val Gly Val
    450                 455                 460

Gln Gly Asp Gly Arg Thr Tyr Gly His Pro Ile Val Leu Arg Pro Val
465                 470                 475                 480

Ser Ser Glu Asp Ala Met Thr Ala Asp Trp Thr Arg Val Pro Tyr Asp
                485                 490                 495

Val Leu Glu Lys Ile Ser Thr Arg Ile Thr Asn Glu Val Asn Asp Val
            500                 505                 510

Asn Arg Val Val Val Asp Ile Thr Ser Lys Pro Pro Gly Thr Ile Glu
        515                 520                 525

Trp Glu
    530
```

<210> SEQ ID NO 2
<211> LENGTH: 1575
<212> TYPE: DNA
<213> ORGANISM: Artificial sequence
<220> FEATURE:
<223> OTHER INFORMATION: Synthetic sequence guaA_c85t

<400> SEQUENCE: 2

```
gtgactcaac ctgcaacaac tccgcgccca gtcctcgtgg tggatttcgg tgcccaatac     60

gcacagctga ttgctcgtcg cgtatgtgag gcatcgattt actccgaggt agtcccacat    120

tccgccaccg ttaaagagat taaagctaaa aaccctgcag ctttgatttt gtccggtggc    180

ccgtcctctg tttatgccga tggcgccccg caattaaagc ctgaactgct cgagcttggt    240

gtgccagtct ttggcatctg ctacggcttc caagccatga accatgcttt gggtggcaac    300

gttgcgcaaa ccggtgaccg tgaatacggc cgcaccgaaa tcacccatac cggtggtgtg    360

ctgcacgacg gcttagaaga aaaccacaag gtctggatgt cccacggtga tgctgtggat    420

aaggcacctg agggctttac cgtgaccgca tcgtcggctg gtgcgccggt tgcagcgatg    480
```

```
gaatgcgtgg ccaagcaaat ggctggtgtg caataccacc ccgaggttat gcattcccca    540

cacggacagg aagtactcgt tcgcttcctc accgaggtag cagggctaga gcagacctgg    600

acctcggcaa atattgcgca gcagcttatc gatgatgtcc gcgcgcaaat cggccctgaa    660

ggccgcgcta tttgtggcct gtcgggcggc gtggactccg cagtcgctgc agcgctcgtg    720

cagcgcgcca ttggcgaccg tttgacctgt gtgttcgtgg accacggtct gctgcgcgcc    780

ggtgagcgtg agcaggtaga aaaggacttc gtggcttcga ctggtgcgaa gctgattacc    840

gcgcatgaag ctgatgcttt cttgtctaag ctcgccggtg ttaccgatcc tgaggctaag    900

cgcaaggcta tcggcgcgga attcatccgt tcctttgagc gtgctgtggc acaggctttg    960

gaagaatctc ctgaagactc cacagtggac ttcctggtcc agggcacctt gtatccggat   1020

gtggttgaat ccggcggcgg tgacggcacc gcaaatatca agtcccacca caatgttggc   1080

ggcctgccag acgatgtcga attcgaactc gtcgagccac tacgcctgct gtttaaggac   1140

gaagtccgtg ccgtcggccg cgagctcggc ctgcctgagg aaatcgttgc ccgccagcca   1200

ttccctggcc ctggcctagg catccgcatc atcggtgaag tcaccgagga gcgtctagaa   1260

atcctgcgtc aagcagacct gattgcgcgt accgagctga ccaacgctgg cctcgacggt   1320

gatatctggc agtgcccagt cgtactgctt gccgatgtcc gctccgtcgg agtccaaggc   1380

gacggccgca cctacggcca cccaatcgtg ctgcgcccag tgtcatccga ggatgccatg   1440

accgccgact ggacccgcgt tccttacgac gtcctagaga aaatctccac ccgcattacc   1500

aacgaagtca acgacgtcaa ccgcgtggtc gtcgacatca cctccaagcc accgggaacc   1560

atcgagtggg agtaa                                                    1575
```

```
<210> SEQ ID NO 3
<211> LENGTH: 530
<212> TYPE: PRT
<213> ORGANISM: Unknown
<220> FEATURE:
<223> OTHER INFORMATION: Corynebacterium stationis

<400> SEQUENCE: 3

Met Thr Gln Pro Ala Thr Thr Pro Arg Pro Val Leu Val Val Asp Phe
1               5                   10                  15

Gly Ala Gln Tyr Ala Gln Leu Ile Ala Arg Arg Val Arg Glu Ala Ser
            20                  25                  30

Ile Tyr Ser Glu Val Val Pro His Ser Ala Thr Val Lys Glu Ile Lys
        35                  40                  45

Ala Lys Asn Pro Ala Ala Leu Ile Leu Ser Gly Gly Pro Ser Ser Val
    50                  55                  60

Tyr Ala Asp Gly Ala Pro Gln Leu Lys Pro Glu Leu Leu Glu Leu Gly
65                  70                  75                  80

Val Pro Val Phe Gly Ile Cys Tyr Gly Phe Gln Ala Met Asn His Ala
                85                  90                  95

Leu Ala Leu Gly Gly Asn Val Ala Gln Thr Gly Asp Arg Glu Tyr Gly
            100                 105                 110

Arg Thr Glu Ile Thr His Thr Gly Gly Val Leu His Asp Gly Leu Glu
        115                 120                 125

Glu Asn His Lys Val Trp Met Ser His Gly Asp Ala Val Asp Lys Ala
    130                 135                 140

Pro Glu Gly Phe Thr Val Thr Ala Ser Ser Ala Gly Ala Pro Val Ala
145                 150                 155                 160
```

```
Ala Met Glu Cys Val Ala Lys Gln Met Ala Gly Val Gln Tyr His Pro
                165                 170                 175

Glu Val Met His Ser Pro His Gly Gln Glu Val Leu Val Arg Phe Leu
            180                 185                 190

Thr Glu Val Ala Gly Leu Glu Gln Thr Trp Thr Ser Ala Asn Ile Ala
        195                 200                 205

Gln Gln Leu Ile Asp Asp Val Arg Ala Gln Ile Gly Pro Glu Gly Arg
    210                 215                 220

Ala Ile Cys Gly Leu Ser Gly Gly Val Asp Ser Ala Val Ala Ala Ala
225                 230                 235                 240

Leu Val Gln Arg Ala Ile Gly Asp Arg Leu Thr Cys Val Phe Val Asp
                245                 250                 255

His Gly Leu Leu Arg Ala Gly Glu Arg Glu Gln Val Glu Lys Asp Phe
            260                 265                 270

Val Ala Leu Ala Ser Thr Gly Ala Lys Leu Ile Thr Ala His Glu Ala
        275                 280                 285

Asp Ala Phe Leu Ser Lys Leu Ala Gly Val Thr Asp Pro Glu Ala Lys
    290                 295                 300

Arg Lys Ala Ile Gly Ala Glu Phe Ile Arg Ser Phe Glu Arg Ala Val
305                 310                 315                 320

Ala Gln Ala Leu Glu Glu Ser Pro Glu Asp Ser Thr Val Asp Phe Leu
                325                 330                 335

Val Gln Gly Thr Leu Tyr Pro Asp Val Val Glu Ser Gly Gly Gly Asp
            340                 345                 350

Gly Thr Ala Asn Ile Lys Ser His His Asn Val Gly Gly Leu Pro Asp
        355                 360                 365

Asp Val Glu Phe Glu Leu Val Glu Pro Leu Arg Leu Leu Phe Lys Asp
    370                 375                 380

Glu Val Arg Ala Leu Ala Val Gly Arg Glu Leu Gly Leu Pro Glu Glu
385                 390                 395                 400

Ile Val Ala Arg Gln Pro Phe Pro Gly Pro Gly Leu Gly Ile Arg Ile
                405                 410                 415

Ile Gly Glu Val Thr Glu Glu Arg Leu Glu Ile Leu Arg Gln Ala Asp
            420                 425                 430

Leu Ile Ala Arg Thr Glu Leu Thr Asn Ala Gly Leu Asp Gly Asp Ile
        435                 440                 445

Trp Gln Cys Pro Val Val Leu Leu Ala Asp Val Arg Ser Val Gly Val
    450                 455                 460

Gln Gly Asp Gly Arg Thr Tyr Gly His Pro Ile Val Leu Arg Pro Val
465                 470                 475                 480

Ser Ser Glu Asp Ala Met Thr Ala Asp Trp Thr Arg Val Pro Tyr Asp
                485                 490                 495

Val Leu Glu Lys Ile Ser Thr Arg Ile Thr Asn Glu Val Asn Asp Val
            500                 505                 510

Asn Arg Val Val Val Asp Ile Thr Ser Lys Pro Pro Gly Thr Ile Glu
        515                 520                 525

Trp Glu
    530
```

<210> SEQ ID NO 4
<211> LENGTH: 1575
<212> TYPE: DNA
<213> ORGANISM: Unknown
<220> FEATURE:
<223> OTHER INFORMATION: Corynebacterium stationis

<400> SEQUENCE: 4
gtgactcaac ctgcaacaac tccgcgccca gtcctcgtgg tggatttcgg tgcccaatac 60
gcacagctga ttgctcgtcg cgtacgtgag gcatcgattt actccgaggt agtcccacat 120
tccgccaccg ttaaagagat taaagctaaa aaccctgcag ctttgatttt gtccggtggc 180
ccgtcctctg tttatgccga tggcgccccg caattaaagc ctgaactgct cgagcttggt 240
gtgccagtct ttggcatctg ctacggcttc caagccatga accatgcttt gggtggcaac 300
gttgcgcaaa ccggtgaccg tgaatacggc cgcaccgaaa tcacccatac cggtggtgtg 360
ctgcacgacg gcttagaaga aaaccacaag gtctggatgt cccacggtga tgctgtggat 420
aaggcacctg agggctttac cgtgaccgca tcgtcggctg gtgcgccggt tgcagcgatg 480
gaatgcgtgg ccaagcaaat ggctggtgtg caataccacc ccgaggttat gcattcccca 540
cacggacagg aagtactcgt tcgcttcctc accgaggtag cagggctaga gcagacctgg 600
acctcggcaa atattgcgca gcagcttatc gatgatgtcc gcgcgcaaat cggccctgaa 660
ggccgcgcta tttgtggcct gtcgggcggc gtggactccg cagtcgctgc agcgctcgtg 720
cagcgcgcca ttggcgaccg tttgacctgt gtgttcgtgg accacggtct gctgcgcgcc 780
ggtgagcgtg agcaggtaga aaaggacttc gtggcttcga ctggtgcgaa gctgattacc 840
gcgcatgaag ctgatgcttt cttgtctaag ctcgccggtg ttaccgatcc tgaggctaag 900
cgcaaggcta tcggcgcgga attcatccgt tcctttgagc gtgctgtggc acaggctttg 960
gaagaatctc ctgaagactc cacagtggac ttcctggtcc agggcacctt gtatccggat 1020
gtggttgaat ccggcggcgg tgacggcacc gcaaatatca agtcccacca caatgttggc 1080
ggcctgccag acgatgtcga attcgaactc gtcgagccac tacgcctgct gtttaaggac 1140
gaagtccgtg ccgtcggccg cgagctcggc ctgcctgagg aaatcgttgc ccgccagcca 1200
ttccctggcc ctggcctagg catccgcatc atcggtgaag tcaccgagga gcgtctagaa 1260
atcctgcgtc aagcagacct gattgcgcgt accgagctga ccaacgctgg cctcgacggt 1320
gatatctggc agtgcccagt cgtactgctt gccgatgtcc gctccgtcgg agtccaaggc 1380
gacggccgca cctacggcca cccaatcgtg ctgcgcccag tgtcatccga ggatgccatg 1440
accgccgact ggacccgcgt tccttacgac gtcctagaga aaatctccac ccgcattacc 1500
aacgaagtca acgacgtcaa ccgcgtggtc gtcgacatca cctccaagcc accgggaacc 1560
atcgagtggg agtaa 1575

<210> SEQ ID NO 5
<211> LENGTH: 18
<212> TYPE: DNA
<213> ORGANISM: Artificial sequence
<220> FEATURE:
<223> OTHER INFORMATION: Primer

<400> SEQUENCE: 5
gcgatgtgat tgccggtg 18

<210> SEQ ID NO 6
<211> LENGTH: 18
<212> TYPE: DNA
<213> ORGANISM: Artificial sequence
<220> FEATURE:
<223> OTHER INFORMATION: Primer

<400> SEQUENCE: 6

-continued gctctaggaa gtcagcag 18

<210> SEQ ID NO 7
<211> LENGTH: 19
<212> TYPE: DNA
<213> ORGANISM: Artificial sequence
<220> FEATURE:
<223> OTHER INFORMATION: Primer

<400> SEQUENCE: 7
tgcccaatac gcacagctg 19

<210> SEQ ID NO 8
<211> LENGTH: 16
<212> TYPE: DNA
<213> ORGANISM: Artificial sequence
<220> FEATURE:
<223> OTHER INFORMATION: Primer

<400> SEQUENCE: 8
ggctggggct ttgtcc 16

<210> SEQ ID NO 9
<211> LENGTH: 18
<212> TYPE: DNA
<213> ORGANISM: Artificial sequence
<220> FEATURE:
<223> OTHER INFORMATION: Primer

<400> SEQUENCE: 9
ggcttagcaa gacctggc 18

<210> SEQ ID NO 10
<211> LENGTH: 37
<212> TYPE: DNA
<213> ORGANISM: Artificial sequence
<220> FEATURE:
<223> OTHER INFORMATION: Primer

<400> SEQUENCE: 10
gtgaattcga gctcggtacc cgcaccgcag ttagccc 37

<210> SEQ ID NO 11
<211> LENGTH: 33
<212> TYPE: DNA
<213> ORGANISM: Artificial sequence
<220> FEATURE:
<223> OTHER INFORMATION: Primer

<400> SEQUENCE: 11
taaatcgatg cctcacatac gcgacgagca atc 33

<210> SEQ ID NO 12
<211> LENGTH: 33
<212> TYPE: DNA
<213> ORGANISM: Artificial sequence
<220> FEATURE:
<223> OTHER INFORMATION: Primer

<400> SEQUENCE: 12
gattgctcgt cgcgtatgtg aggcatcgat tta 33

<210> SEQ ID NO 13
<211> LENGTH: 39
<212> TYPE: DNA
<213> ORGANISM: Artificial sequence
<220> FEATURE:
<223> OTHER INFORMATION: Primer

<400> SEQUENCE: 13
ggtcgactct agaggatccc ccgaggtcca ggtctgctc 39

<210> SEQ ID NO 14
<211> LENGTH: 17
<212> TYPE: DNA
<213> ORGANISM: Artificial sequence
<220> FEATURE:
<223> OTHER INFORMATION: Primer

<400> SEQUENCE: 14
ggaatccgaa gcggagc 17

<210> SEQ ID NO 15
<211> LENGTH: 18
<212> TYPE: DNA
<213> ORGANISM: Artificial sequence
<220> FEATURE:
<223> OTHER INFORMATION: Primer

<400> SEQUENCE: 15
caggccacaa atagcgcg 18

<210> SEQ ID NO 16
<211> LENGTH: 33
<212> TYPE: DNA
<213> ORGANISM: Artificial sequence
<220> FEATURE:
<223> OTHER INFORMATION: Primer

<400> SEQUENCE: 16
taaatcgatg cctcgcctac gcgacgagca atc 33

<210> SEQ ID NO 17
<211> LENGTH: 33
<212> TYPE: DNA
<213> ORGANISM: Artificial sequence
<220> FEATURE:
<223> OTHER INFORMATION: Primer

<400> SEQUENCE: 17
gattgctcgt cgcgtaggcg aggcatcgat tta 33

<210> SEQ ID NO 18
<211> LENGTH: 33
<212> TYPE: DNA
<213> ORGANISM: Artificial sequence
<220> FEATURE:
<223> OTHER INFORMATION: Primer

<400> SEQUENCE: 18
taaatcgatg cctcgaatac gcgacgagca atc 33

<210> SEQ ID NO 19
<211> LENGTH: 33
<212> TYPE: DNA
<213> ORGANISM: Artificial sequence
<220> FEATURE:
<223> OTHER INFORMATION: Primer

<400> SEQUENCE: 19
gattgctcgt cgcgtattcg aggcatcgat tta 33

<210> SEQ ID NO 20
<211> LENGTH: 33
<212> TYPE: DNA
<213> ORGANISM: Artificial sequence
<220> FEATURE:
<223> OTHER INFORMATION: Primer

<400> SEQUENCE: 20
taaatcgatg cctcggatac gcgacgagca atc 33

<210> SEQ ID NO 21
<211> LENGTH: 33
<212> TYPE: DNA
<213> ORGANISM: Artificial sequence
<220> FEATURE:
<223> OTHER INFORMATION: Primer

<400> SEQUENCE: 21
gattgctcgt cgcgtatccg aggcatcgat tta 33

<210> SEQ ID NO 22
<211> LENGTH: 33
<212> TYPE: DNA
<213> ORGANISM: Artificial sequence
<220> FEATURE:
<223> OTHER INFORMATION: Primer

<400> SEQUENCE: 22
taaatcgatg cctcgtatac gcgacgagca atc 33

<210> SEQ ID NO 23
<211> LENGTH: 33
<212> TYPE: DNA
<213> ORGANISM: Artificial sequence
<220> FEATURE:
<223> OTHER INFORMATION: Primer

<400> SEQUENCE: 23
gattgctcgt cgcgtatacg aggcatcgat tta 33

<210> SEQ ID NO 24
<211> LENGTH: 33
<212> TYPE: DNA
<213> ORGANISM: Artificial sequence
<220> FEATURE:
<223> OTHER INFORMATION: Primer

<400> SEQUENCE: 24
taaatcgatg cctcccatac gcgacgagca atc 33

<210> SEQ ID NO 25
<211> LENGTH: 33
<212> TYPE: DNA
<213> ORGANISM: Artificial sequence
<220> FEATURE:
<223> OTHER INFORMATION: Primer

<400> SEQUENCE: 25
gattgctcgt cgcgtatggg aggcatcgat tta 33

<210> SEQ ID NO 26
<211> LENGTH: 33
<212> TYPE: DNA
<213> ORGANISM: Artificial sequence
<220> FEATURE:
<223> OTHER INFORMATION: Primer

<400> SEQUENCE: 26
taaatcgatg cctcgattac gcgacgagca atc 33

<210> SEQ ID NO 27
<211> LENGTH: 33
<212> TYPE: DNA
<213> ORGANISM: Artificial sequence
<220> FEATURE:
<223> OTHER INFORMATION: Primer

<400> SEQUENCE: 27
gattgctcgt cgcgtaatcg aggcatcgat tta 33

<210> SEQ ID NO 28
<211> LENGTH: 33
<212> TYPE: DNA
<213> ORGANISM: Artificial sequence
<220> FEATURE:
<223> OTHER INFORMATION: Primer

<400> SEQUENCE: 28
taaatcgatg cctccactac gcgacgagca atc 33

<210> SEQ ID NO 29
<211> LENGTH: 33
<212> TYPE: DNA
<213> ORGANISM: Artificial sequence
<220> FEATURE:
<223> OTHER INFORMATION: Primer

<400> SEQUENCE: 29
gattgctcgt cgcgtagtgg aggcatcgat tta 33

<210> SEQ ID NO 30
<211> LENGTH: 33
<212> TYPE: DNA
<213> ORGANISM: Artificial sequence
<220> FEATURE:
<223> OTHER INFORMATION: Primer

<400> SEQUENCE: 30
taaatcgatg cctctggtac gcgacgagca atc 33

<210> SEQ ID NO 31
<211> LENGTH: 33
<212> TYPE: DNA
<213> ORGANISM: Artificial sequence
<220> FEATURE:
<223> OTHER INFORMATION: Primer

<400> SEQUENCE: 31
gattgctcgt cgcgtaccag aggcatcgat tta 33

<210> SEQ ID NO 32
<211> LENGTH: 33
<212> TYPE: DNA
<213> ORGANISM: Artificial sequencer
<220> FEATURE:
<223> OTHER INFORMATION: Primer

<400> SEQUENCE: 32
taaatcgatg cctcggttac gcgacgagca atc 33

<210> SEQ ID NO 33

<211> LENGTH: 33
<212> TYPE: DNA
<213> ORGANISM: Artificial sequence
<220> FEATURE:
<223> OTHER INFORMATION: Primer

<400> SEQUENCE: 33
gattgctcgt cgcgtaaccg aggcatcgat tta 33

<210> SEQ ID NO 34
<211> LENGTH: 33
<212> TYPE: DNA
<213> ORGANISM: Artificial sequence
<220> FEATURE:
<223> OTHER INFORMATION: Primer

<400> SEQUENCE: 34
taaatcgatg cctctgctac gcgacgagca atc 33

<210> SEQ ID NO 35
<211> LENGTH: 33
<212> TYPE: DNA
<213> ORGANISM: Artificial sequence
<220> FEATURE:
<223> OTHER INFORMATION: Primer

<400> SEQUENCE: 35
gattgctcgt cgcgtagcag aggcatcgat tta 33

<210> SEQ ID NO 36
<211> LENGTH: 33
<212> TYPE: DNA
<213> ORGANISM: Artificial sequence
<220> FEATURE:
<223> OTHER INFORMATION: Primer

<400> SEQUENCE: 36
taaatcgatg cctcatctac gcgacgagca atc 33

<210> SEQ ID NO 37
<211> LENGTH: 33
<212> TYPE: DNA
<213> ORGANISM: Artificial sequence
<220> FEATURE:
<223> OTHER INFORMATION: Primer

<400> SEQUENCE: 37
gattgctcgt cgcgtagatg aggcatcgat tta 33

<210> SEQ ID NO 38
<211> LENGTH: 33
<212> TYPE: DNA
<213> ORGANISM: Artificial sequence
<220> FEATURE:
<223> OTHER INFORMATION: Primer

<400> SEQUENCE: 38
taaatcgatg cctcgtttac gcgacgagca atc 33

<210> SEQ ID NO 39
<211> LENGTH: 33
<212> TYPE: DNA
<213> ORGANISM: Artificial sequence
<220> FEATURE:
<223> OTHER INFORMATION: Primer

<400> SEQUENCE: 39
gattgctcgt cgcgtaaacg aggcatcgat tta 33

<210> SEQ ID NO 40
<211> LENGTH: 33
<212> TYPE: DNA
<213> ORGANISM: Artificial sequence
<220> FEATURE:
<223> OTHER INFORMATION: Primer

<400> SEQUENCE: 40
taaatcgatg cctcgtgtac gcgacgagca atc 33

<210> SEQ ID NO 41
<211> LENGTH: 33
<212> TYPE: DNA
<213> ORGANISM: Artificial sequence
<220> FEATURE:
<223> OTHER INFORMATION: Primer

<400> SEQUENCE: 41
gattgctcgt cgcgtacacg aggcatcgat tta 33

<210> SEQ ID NO 42
<211> LENGTH: 33
<212> TYPE: DNA
<213> ORGANISM: Artificial sequence
<220> FEATURE:
<223> OTHER INFORMATION: Primer

<400> SEQUENCE: 42
taaatcgatg cctccagtac gcgacgagca atc 33

<210> SEQ ID NO 43
<211> LENGTH: 33
<212> TYPE: DNA
<213> ORGANISM: Artificial sequence
<220> FEATURE:
<223> OTHER INFORMATION: Primer

<400> SEQUENCE: 43
gattgctcgt cgcgtactgg aggcatcgat tta 33

<210> SEQ ID NO 44
<211> LENGTH: 33
<212> TYPE: DNA
<213> ORGANISM: Artificial sequence
<220> FEATURE:
<223> OTHER INFORMATION: Primer

<400> SEQUENCE: 44
taaatcgatg cctccattac gcgacgagca atc 33

<210> SEQ ID NO 45
<211> LENGTH: 33
<212> TYPE: DNA
<213> ORGANISM: Artificial sequence
<220> FEATURE:
<223> OTHER INFORMATION: Primer

<400> SEQUENCE: 45
gattgctcgt cgcgtaatgg aggcatcgat tta 33

<210> SEQ ID NO 46
<211> LENGTH: 33
<212> TYPE: DNA

```
<213> ORGANISM: Artificial sequence
<220> FEATURE:
<223> OTHER INFORMATION: Primer

<400> SEQUENCE: 46

taaatcgatg cctcctgtac gcgacgagca atc                                    33


<210> SEQ ID NO 47
<211> LENGTH: 33
<212> TYPE: DNA
<213> ORGANISM: Artificial sequence
<220> FEATURE:
<223> OTHER INFORMATION: Primer

<400> SEQUENCE: 47

gattgctcgt cgcgtacagg aggcatcgat tta                                    33


<210> SEQ ID NO 48
<211> LENGTH: 33
<212> TYPE: DNA
<213> ORGANISM: Artificial sequence
<220> FEATURE:
<223> OTHER INFORMATION: Primer

<400> SEQUENCE: 48

taaatcgatg cctcctttac gcgacgagca atc                                    33


<210> SEQ ID NO 49
<211> LENGTH: 33
<212> TYPE: DNA
<213> ORGANISM: Artificial sequence
<220> FEATURE:
<223> OTHER INFORMATION: Primer

<400> SEQUENCE: 49

gattgctcgt cgcgtaaagg aggcatcgat tta                                    33


<210> SEQ ID NO 50
<211> LENGTH: 33
<212> TYPE: DNA
<213> ORGANISM: Artificial sequence
<220> FEATURE:
<223> OTHER INFORMATION: Primer

<400> SEQUENCE: 50

taaatcgatg cctcttctac gcgacgagca atc                                    33


<210> SEQ ID NO 51
<211> LENGTH: 33
<212> TYPE: DNA
<213> ORGANISM: Artificial sequence
<220> FEATURE:
<223> OTHER INFORMATION: Primer

<400> SEQUENCE: 51

gattgctcgt cgcgtagaag aggcatcgat tta                                    33
```

GLUTAMINE-HYDROLYZING GMP SYNTHASE VARIANT AND METHOD FOR PRODUCING PURINE NUCLEOTIDE BY USING SAME

STATEMENT REGARDING THE SEQUENCE LISTING

The Sequence Listing associated with this application is provided in text format in lieu of a paper copy, and is hereby incorporated by reference into the specification. The name of the text file containing the Sequence Listing is 200187_489 USPC_SEQUENCE_LISTING.txt. The text file is 22508 bytes, was created on Aug. 1, 2022 and is being submitted electronically via EFS-Web.

TECHNICAL FIELD

The present disclosure relates to a glutamine-hydrolyzing GMP synthase variant and a method for producing a purine nucleotide by using the same.

BACKGROUND ART

Purine nucleotides, which are a type of nucleic acid-based materials, are widely used for food seasoning additives or food and are receiving attention as a flavor-enhancing nucleic acid-based seasonings.

For the production of purine nucleotides, various studies have been conducted to develop microorganisms with high-efficiency production and fermentation process technology. For example, target substance-specific approaches are mainly used, such as increasing the expression of genes encoding enzymes involved in biosynthesis of purine nucleotides or removing unnecessary genes in the biosynthesis (EP 3722430 A1 and US 2020-0347346 A1).

As the demand for purine nucleotides increases, studies for effective purine nucleotide production are still needed.

DISCLOSURE

Technical Problem

The present disclosure provides a glutamine-hydrolyzing GMP synthase variant.

Technical Solution

An aspect of the present disclosure is to provide a glutamine-hydrolyzing GMP synthase variant.

Another aspect of the present disclosure is to provide a polynucleotide encoding the variant.

Still another aspect of the present disclosure is to provide a microorganism containing the variant or the polynucleotide encoding the same.

Still another aspect of the disclosure is to provide a method for producing a purine nucleotide, the method including culturing the microorganism.

Advantageous Effects

The variants of the present disclosure can be used to produce purine nucleotides with high efficiency.

DETAILED DESCRIPTION OF THE INVENTION

The present disclosure will be specifically described as follows. Each description and embodiment disclosed in this disclosure may also be applied to other descriptions and embodiments. That is, all combinations of various elements disclosed in this disclosure fall within the scope of the present disclosure. Furthermore, the scope of the present disclosure is not limited by the specific description below. Furthermore, throughout the entire specification, many papers and patent documents are referenced, and their citations are provided. The disclosures of cited papers and patent documents are incorporated into the present specification in their entirety by reference, and the level of the technical field within which the present disclosure falls and details of the present disclosure are explained more clearly.

An aspect of the present disclosure provides a glutamine-hydrolyzing GMP synthase variant in which the amino acid corresponding to position 29 in SEQ ID NO: 3 is substituted with another amino acid.

The glutamine-hydrolyzing GMP synthase variant refers to a variant including a substitution of the amino acid corresponding to position 29 from the N-terminus of SEQ ID NO: 3 with another amino acid, in a polypeptide having glutamine-hydrolyzing GMP synthase activity or a glutamine-hydrolyzing GMP synthase.

In the present disclosure, "glutamine-hydrolyzing GMP synthase" is an enzyme involved in the conversion of 5'-xanthosine monophosphate (XMP) into 5'-guanosine monophosphate (hereinafter, GMP).

The glutamine-hydrolyzing GMP synthase of the present disclosure may be glutamine-hydrolyzing GMP synthase or a polypeptide having glutamine-hydrolyzing GMP synthase activity, which is to be modified to prepare a glutamine-hydrolyzing GMP synthase variant provided in the present disclosure.

Specifically, the polypeptide may be a naturally occurring polypeptide or a wild-type polypeptide, or a mature polypeptide thereof, and may include a variant or functional fragment thereof, but any polypeptide is included without limitation as long as it can be a parent of the glutamine-hydrolyzing GMP synthase variant of the present disclosure.

In an embodiment, the glutamine-hydrolyzing GMP synthase of the present disclosure may be derived from the genus *Corynebacterium*, and more specifically *Corynebacterium stationis*, but is not limited thereto.

In an embodiment, the glutamine-hydrolyzing GMP synthase of the present disclosure may be the polypeptide of SEQ ID NO: 3. In an embodiment, the glutamine-hydrolyzing GMP synthase of the present disclosure may be a polypeptide having at least about 60%, 70%, 75%, 80%, 85%, 90%, 93%, 95%, 96%, 97%, 98%, or 99% sequence identity with the polypeptide of SEQ ID NO: 3, and any polypeptide that has activity identical or corresponding to that of a polypeptide consisting of the amino acid sequence of SEQ ID NO: 3 is included, without limitation, within a range of glutamine-hydrolyzing GMP synthase. Specifically, the glutamine-hydrolyzing GMP synthase may have, contain, or consist essentially of the amino acid sequence set forth in SEQ ID NO: 3, but is not limited thereto.

The glutamine-hydrolyzing GMP synthase to be mutated in the present disclosure may be *Corynebacterium* sp.-derived glutamine-hydrolyzing GMP synthase, and specifically, a polypeptide/protein containing the amino acid sequence set forth in SEQ ID NO: 3 or any polypeptide/protein having the same activity as the synthase may be included without limitation. For example, the polypeptide/protein may contain the amino acid sequence of SEQ ID NO: 3 or an amino acid sequence having at least 80% homology or identity therewith, but is not limited thereto. Specifically, the polypeptide/protein may contain an amino acid sequence having at least 80%, 85%, 90%, 95%, 96%, 97%, 98%, or 99% homology or identity with SEQ ID NO: 3. A polypeptide/protein having deletion, modification, substitution, or addition in a part of the sequence thereof is obviously included within a range of the polypeptide/protein to be mutated in the present disclosure as long as it is a polypeptide/protein having such homology or identity and exhibiting glutamine-hydrolyzing GMP synthase activity.

The sequence of the glutamine-hydrolyzing GMP synthase of the present disclosure may be available in the NCBI GenBank, a known database. For example, the glutamine-hydrolyzing GMP synthase of the present disclosure may be the polypeptide encoded by guaA gene. For example, the glutamine-hydrolyzing GMP synthase of the present disclosure may be derived from *Corynebacterium stationis, Corynebacterium casei*, or *Corynebacterium ammoniagenes*, and examples thereof may be an enzyme expressed by NCBI Reference sequence WP_194285183.1, WP_006823296.1, or WP_040355890.1, but is not limited thereto.

As used herein, the term "homology" or "identity" refers to the degree of similarity between two given amino acid sequences or nucleotide sequences and may be expressed as a percentage. The terms homology and identity may be often used interchangeably.

The sequence homology or identity of conserved polynucleotides or polypeptides may be determined by a standard alignment algorithm, and default gap penalties established by a program to be used may be used together. Substantially, homologous or identical sequences may generally hybridize with each other as a whole or in part under moderate or highly stringent conditions. It is obvious that the hybridization also includes hybridization with a polynucleotide containing usual codons or codons considering codon degeneracy in the polynucleotide.

The homology, similarity, or identity between any two polynucleotide or polypeptide sequences may be determined using a known computer algorithm, such as the "FASTA" program, by using default parameters as in Pearson et al., (1988) *Proc. Natl. Acad. Sci. USA* 85:2444. Alternatively, the homology, similarity, or identity may be determined using the Needleman-Wunsch algorithm (Needleman and Wunsch, 1970, *J. Mol. Biol.* 48:443-453), which is performed in the Needleman program of the European Molecular Biology Open Software Suite (EMBOSS) package (including Rice et al., 2000, *Trends Genet.* 16:276-277) (version 5.0.0 or later) (GCG program package (Devereux, J. et al., *Nucleic Acids Research* 12:387 (1984)), BLASTP, BLASTN, FASTA (Atschul, S. F. et al., *J MOLEC BIOL* 215:403 (1990); *Guide to Huge Computers*, Martin J. Bishop, ed., Academic Press, San Diego, 1994, and CARILLO et al. (1988) *SIAM J Applied Math* 48:1073). For example, the homology, similarity, or identity may be determined using BLAST or ClustalW from the National Center for Biotechnology Information database.

The homology, similarity, or identity between polynucleotides or polypeptides may be determined by comparing sequence information using the GAP computer program as introduced by, for example, Needleman et al. (1970), *J Mol Biol.* 48:443 as disclosed by Smith and Waterman, *Adv. Appl. Math* (1981) 2:482. Briefly, the GAP program defines the homology, similarity, or identity as the value obtained by dividing the number of similarly aligned symbols (i.e., nucleotides or amino acids) by the total number of the symbols in the shorter of the two sequences. The default parameters for the GAP program may include: (1) a binary comparison matrix (containing a value 1 for identity and a value 0 for non-identity) and the weighted comparison matrix of Gribskov et al (1986) *Nucl. Acids Res.* 14: 6745 as disclosed in Schwartz and Dayhoff, eds., *Atlas of Protein Sequence and Structure*, National Biomedical Research Foundation, pp. 353-358 (1979) (or EDNAFULL (EMBOSS version of NCBI NUC4.4) substitution matrix); (2) a penalty of 3.0 for each gap and an additional 0.10 penalty for each symbol in each gap (or a gap open penalty of 10 and a gap extension penalty of 0.5); and (3) no penalty for end gaps.

As used herein, the term "variant" refers to a polypeptide which has a different sequence but maintain functions or properties compared with the amino acid sequence prior to mutation by conservative substitution and/or modification of at least one amino acid. Such a variant can be usually identified by modifying one or more amino acids in the amino acid sequence of the polypeptide and evaluating the properties of the modified polypeptide. That is, the ability of the variant may be increased, unchanged, or reduced compared with that of a polypeptide prior to mutation. Some variants may include a variant in which at least one part, such as an N-terminal leader sequence or a transmembrane domain, is removed. Other variants may include a variant in which a part of the N-terminus and/or C-terminus of a mature protein is removed. The term "variant" may also be used interchangeably with "modification", "modified protein", "modified polypeptide", "mutant", "mutein", "divergent", or the like, and any term that is used in a sense of being mutated can be used without limitation thereto.

In addition, the variant may include deletions or additions of amino acids that have a minimal effect on the properties and secondary structures of a polypeptide. For example, a signal (or leader) sequence of the N-terminus of a protein which co-translationally or post-translationally directs transfer of the protein may be conjugated to the N-terminus of the variant. In addition, the variant may also be conjugated to another sequence or a linker so that the variant is identified, purified, or synthesized.

The glutamine-hydrolyzing GMP synthase variant provided in the present disclosure may be a polypeptide containing the amino acid sequence in which the amino acid corresponding to position 29 in SEQ ID NO: 3 is substituted with another amino acid. Specifically, the other amino acid may be selected from glycine, alanine, valine, leucine, isoleucine, methionine, phenylalanine, tryptophan, proline, serine, threonine, cysteine, tyrosine, asparagine, glutamine, aspartic acid, glutamic acid, lysine, and histidine.

The "another amino acid" is not limited as long as the amino acid differs from the amino acid prior to substitution. The expression "substituted with a particular amino acid" in the present disclosure is obvious as being substituted with an amino acid different from the amino acid prior to substitution even though "substituted with another amino acid" is not specifically stated.

In an embodiment, the variant of the present disclosure may be a variant in which the amino acid corresponding to position 29 in the amino acid sequence of SEQ ID NO: 3 as a reference protein is an amino acid except for arginine. Specifically, the amino acid corresponding to position 29 in SEQ ID NO: 3 of the variant may be selected from glycine, alanine, valine, leucine, isoleucine, methionine, phenylalanine, tryptophan, proline, serine, threonine, cysteine, tyrosine, asparagine, glutamine, aspartic acid, glutamic acid, lysine, and histidine.

In an embodiment, the glutamine-hydrolyzing GMP synthase variant of the present disclosure may contain an amino acid sequence in which the amino acid corresponding to position 29 in the amino acid sequence set forth in SEQ ID NO: 3 is an amino acid except for arginine and which has at least 70%, 75%, 80%, 85%, 90%, 95%, 96%, 97%, 98%, 99%, 99.5%, 99.7%, or 99.8% homology or identity with the amino acid sequence set forth in SEQ ID NO: 3.

For example, the glutamine-hydrolyzing GMP synthase variant of the present disclosure may consist of the amino acid sequence of SEQ ID NO: 1 or may contain an amino acid sequence having at least 70%, 75%, 80%, 85%, 90%, 95%, 96%, 97%, 98%, 99%, 99.5%, 99.7%, or 99.8% identity therewith, but is not limited thereto.

It is obvious that even a variant having an amino acid sequence with deletion, modification, substitution, conservative substitution, or addition in a part thereof may also be included within the scope of the present disclosure as long as the amino acid sequence has such homology or identity and exhibits activity corresponding to the variant of the present disclosure.

For example, there may be sequence addition or deletion, naturally occurring mutation, silent mutation, or conservative substitution, which does not alter functions of the variant of the present disclosure, in the N-terminus, C-terminus, and/or inside of the amino acid sequence.

The "conservative substitution" refers to a substitution of one amino acid with another amino acid having similar structural and/or chemical properties thereto. Such an amino acid substitution may generally occur on the basis of similarities in polarity, charge, solubility, hydrophobicity, hydrophilicity, and/or amphipathic nature of residues. Usually, the conservative substitution may have little or no effect on the activity of a protein or a polypeptide.

As used herein, the term "corresponding to" refers to an amino acid residue at a position recited in a polypeptide, or an amino acid residue similar, identical, or homologous to a residue recited in a polypeptide. Identifying an amino acid at a corresponding position may be determining a particular amino acid of a sequence referring to a particular sequence. As used herein, the term "corresponding region" generally refers to a similar or corresponding site in a related protein or reference protein.

For example, any amino acid sequence is aligned with SEQ ID NO: 3, and based on this, each amino acid residue of the amino acid sequence may be numbered with reference to an amino acid residue numerical position corresponding to an amino acid residue of SEQ ID NO: 3. For example, a sequence alignment algorithm as described in the present disclosure may identify the position of an amino acid or a position of occurrence of modifications, such as substitution, insertion, or deletion, compared with a query sequence (also referred to as a "reference sequence").

For such alignment, Needleman-Wunsch algorithm (Needleman and Wunsch, 1970, *J. Mol. Biol.* 48:443-453) or Needle program of the EMBOSS package (EMBOSS: The European Molecular Biology Open Software Suite, Rice et al., 2000, *Trends Genet.* 16:276-277) may be for example used, but without limitation thereto, a sequence alignment program, a pairwise sequence comparison algorithm, or the like, which are known in the art, may be used as appropriate.

Another aspect of the present disclosure provides a polynucleotide encoding the variant of the present disclosure.

As used herein, the term "polynucleotide" refers to a DNA or RNA strand having more than a certain length as a nucleotide polymer which is a long chain of nucleotide monomers linked by covalent bonds.

For example, the polynucleotide encoding the glutamine-hydrolyzing GMP synthase of the present disclosure may have or contain a sequence encoding the nucleotide sequence of SEQ ID NO: 4. For example, the polynucleotide encoding the glutamine-hydrolyzing GMP synthase may consist or consist essentially of the sequence of SEQ ID NO: 4.

The polynucleotide of the present disclosure may be variously modified in a coding region thereof within a range in which the amino acid sequence of the variant of the present disclosure is not changed, considering codon degeneracy, or codons preferred by an organism in which the variant of the present disclosure is to be expressed.

Specifically, the polynucleotide encoding the glutamine-hydrolyzing GMP synthase variant of the present disclosure may have or contain a nucleotide sequence having at least 70%, at least 75%, at least 80%, at least 85%, at least 90%, at least 95%, at least 96%, at least 97%, at least 98%, at least 99%, and less than 100% homology or identity with the sequence of SEQ ID NO: 4, or may consist or consist essentially of a nucleotide sequence having at least 70%, at least 75%, at least 80%, at least 85%, at least 90%, at least 95%, at least 96%, at least 97%, at least 98%, and less than 100% homology or identity with the sequence of SEQ ID NO: 4, but is not limited thereto. In the sequences having such homology or identity, a codon encoding the amino acid corresponding to position 29 in SEQ ID NO: 3 may be one of the codons encoding amino acids except for arginine.

In addition, the polynucleotide of the present disclosure may include, without limitation, a sequence that can hydride, under stringent conditions, with a probe capable of being prepared from a known gene sequence, for example, a sequence complementary to a part or the entirety of the polynucleotide sequence of the present disclosure. The term "stringent condition" refers to a condition that enables specific hybridization between polynucleotides. These conditions are described in detail in the literature (see J. Sambrook et al., *Molecular Cloning, A Laboratory Manual,* 2nd Edition, Cold Spring Harbor Laboratory press, Cold Spring Harbor, New York, 1989; and F. M. Ausubel et al., *Current Protocols in Molecular Biology*, John Wiley & Sons, Inc., New York, 9.50-9.51, 11.7-11.8). For example, such conditions may include conditions under which polynucleotides having high homology or identity, such as polynucleotides having at least 70%, at least 75%, at least 80%, at least 85%, at least 90%, at least 95%, at least 96%, at least 97%, at least 98%, or at least 99% homology or identity therebetween, hybridize with each other, but polynucleotides having lower homology or identity do not hybridize with each other; or washing conditions for typical Southern hybridization, in which washing is conducted at a salt concentration and a temperature, corresponding to 60° C., 1×SSC, 0.1% SDS; specifically 60° C., 0.1×SSC, 0.1% SDS; and more specifically 68° C., 0.1×SSC, 0.1% SDS, once, specifically twice or three times.

Hybridization requires that two nucleic acids have complementary sequences, although mismatches between bases may be possible depending on hybridization stringency. The term "complementary" is used to describe the relationship between nucleotide bases that can hybridize with each another. For example, as for DNA, adenine is complementary to thymine and cytosine is complementary to guanine. Therefore, the polynucleotide of the present disclosure may also include isolated nucleic acid fragments complementary to the entire sequence as well as to substantially similar nucleic acid sequences.

Specifically, a polynucleotide having homology or identity with the polynucleotide of the present disclosure may be detected using hybridization conditions including a step of hybridization at $T_m$ of 55° C. and utilizing the above-described conditions. In addition, the $T_m$ value may be 60°

C., 63° C., or 65° C., but is not limited thereto, and may be appropriately controlled by a person skilled in the art according to the purpose.

The appropriate stringency for hybridizing polynucleotides depends on the length of the polynucleotides and the degree of complementarity, and variables thereof are well known in the art (e.g., Sambrook et al., supra).

Still another aspect of the present disclosure provides a vector including the polynucleotide encoding the variant of the present disclosure. The vector may be an expression vector for expressing the polynucleotide in a host cell, but is not limited thereto.

The "vector" of the present disclosure may include a DNA construct containing the nucleotide sequence of a polynucleotide, encoding a target polypeptide, operatively linked to a suitable expression control region (or expression control sequence) so as to express the target polypeptide in an appropriate host. The expression control region may include a promoter capable of initiating transcription, any operator sequence for controlling such transcription, a sequence for encoding a suitable mRNA ribosomal binding site, and a sequence for controlling the termination of transcription and translation. The vector, after transformation into an appropriate host cell, can replicate or function independently of the genome of the host, or may be integrated into the genome itself.

The vector used in the present disclosure is not particularly limited, and any vector known in the art may be used. Examples of the vector that is usually used may include native or recombinant plasmids, cosmids, viruses, and bacteriophages. For example, pWE15, M13, MBL3, MBL4, IXII, ASHII, APII, t10, t11, Charon4A, and Charon21A may be used as phage vectors or cosmid vectors, and pBR-based, pUC-based, pBluescriptII-based, pGEM-based, pTZ-based, pCL-based, and pET-based vectors may be used as plasmid vectors. Specifically, pDZ, pDC, pDCM2, pACYC177, pACYC184, pCL, pECCG117, pUC19, pBR322, pMW118, and pCC1BAC vectors may be used.

For example, a polynucleotide encoding a target polypeptide may be inserted in the chromosome through a vector for chromosomal insertion in a cell. The insertion of the polynucleotide into the chromosome may be performed using any method known in the art, for example, homologous recombination, but is not limited thereto. The vector may further include a selection maker for investigating the insertion or non-insertion of the chromosome. The selection marker is for selecting cells transformed with the vector, that is, identifying the insertion of a target nucleic acid molecule, and markers imparting a selectable phenotype, such as drug resistance, auxotrophy, cytotoxic drug resistance, or expression of surface protein may be used. Under the circumstances of the treatment with a selective agent, only the cells expressing selection markers can survive or express other phenotypic traits, so that the transformed cells can be selected.

As used herein, the term "transformation" means that a vector containing a polynucleotide encoding a target polypeptide is introduced into a host cell or microorganism to allow the polypeptide encoded by the polynucleotide to be expressed in the host cell. Examples of the transformed polynucleotide may include any polypeptide as long as it can be expressed in a host cell, regardless of whether it is inserted and located into the chromosome of the host cell or located outside of the chromosome. In addition, examples of the polynucleotide include DNA and/or RNA encoding a target protein. The polynucleotide may be introduced in any form as long as the polynucleotide can be introduced and expressed in a host cell. For example, the polynucleotide may be introduced in the form of an expression cassette, which is a gene construct containing all factors required for self-expression. The expression cassette may generally include a promoter operatively linked to the polynucleotide, a transcription termination signal, a ribosome binding site, and a translation terminal signal. The expression cassette may be an expression vector enabling self-replication. In addition, the polynucleotide may be introduced in the form as it is into the host cell to be operatively linked to the sequence required for expression in the host cell, but is not limited thereto.

As above, the term "operatively linked" refers to a functional linkage between a promoter sequence for initiating and mediating the transcription of the polynucleotide encoding the variant of the present disclosure and the polynucleotide sequence.

Still another aspect of the present disclosure provides a microorganism including the variant of the present disclosure or the polynucleotide encoding the variant.

The microorganism of the present disclosure may include the variant of the present disclosure, a polynucleotide encoding the variant, or a vector including the polynucleotide.

As used herein, the term "microorganism (or strain)" encompasses all of wild-type microorganisms or naturally or artificially genetically modified microorganisms, refers to a microorganism in which a particular mechanism is diminished or enhanced due to the insertion of an exogenous gene or the enhancement or inactivation of activity of an endogenous gene, and may be a microorganism including a genetic modification for production of a target polypeptide, protein, or product.

The microorganism of the present disclosure may be: a microorganism including at least one of the variant of the present disclosure, a polynucleotide encoding the variant of the present disclosure, and a vector including the polynucleotide encoding the variant of the present disclosure; a microorganism modified to express the variant of the present disclosure or the polynucleotide encoding the variant of the present disclosure; a microorganism (e.g., recombinant strain) expressing the variant of the present disclosure or a polynucleotide encoding the variant of the present disclosure; or a microorganism (e.g., recombinant strain) having activity of the variant of the present disclosure, but is not limited thereto.

The microorganisms of the present disclosure may have purine nucleotide-producing ability.

The microorganism of the present disclosure may be a microorganism naturally having glutamine-hydrolyzing GMP synthase or purine nucleotide-producing ability, or a microorganism obtained by introducing the variant of the present disclosure or a polynucleotide encoding the same (or a vector including the polynucleotide) into a parent strain without glutamine-hydrolyzing GMP synthase or purine nucleotide-producing ability and/or by imparting purine nucleotide-producing ability to the parent strain, but is not limited thereto. For example, the microorganism of the present disclosure may be a microorganism having purine nucleotide-producing ability imparted by the introduction of the glutamine-hydrolyzing GMP synthase variant of the present disclosure. For example, the microorganism of the present disclosure may be a microorganism having purine nucleotide-producing ability enhanced by the introduction of the glutamine-hydrolyzing GMP synthase variant of the present disclosure. However, the microorganism of the present disclosure is not limited thereto.

For example, the strain of the present disclosure is a cell or microorganism transformed by a vector including the polynucleotide of the present disclosure or a polynucleotide encoding the variant of the present disclosure, and thus expresses the variant of the present disclosure, and for the purpose of the present disclosure, the strain of the present disclosure encompasses all the microorganisms that can produce a purine nucleotide by including the variant of the present disclosure. For example, the strain of the present disclosure may be a recombinant strain having enhanced purine nucleotide-producing ability through the expression of the glutamine-hydrolyzing GMP synthase variant by introducing a polynucleotide encoding the variant of the present disclosure into a native wild-type microorganism or a microorganism producing a purine nucleotide. The recombinant strain having enhanced purine nucleotide-producing ability compared with a native wild-type microorganism or a glutamine-hydrolyzing GMP synthase non-modified microorganism (i.e., a microorganism expressing wild-type glutamine-hydrolyzing GMP synthase (SEQ ID NO: 3) or a microorganism not expressing a modified protein), but is not limited thereto.

As used herein, the term "non-modified microorganism" may refer to a wild-type strain or a native strain as it is, or a strain before transformation due to genetic mutation caused by natural or artificial factors, not excluding strains including mutations that may naturally occur in microorganisms. For example, the non-modified microorganism may refer to a strain to which the glutamine-hydrolyzing GMP synthase variant described herein is not introduced or before the introduction thereof. The "non-modified microorganism" may be used interchangeably with "strain before modification", "microorganism before modification", "non-varied strain", "non-modified strain", "non-varied microorganism", or "reference microorganism".

In an embodiment, the microorganism of the present disclosure may be a microorganism of the genus *Corynebacterium*. For example, the microorganism of the present disclosure may be *Corynebacterium stationis, Corynebacterium crudilactis, Corynebacterium deserti, Corynebacterium efficiens, Corynebacterium callunae, Corynebacterium glutamicum, Corynebacterium singulare, Corynebacterium halotolerans, Corynebacterium striatum, Corynebacterium ammoniagenes, Corynebacterium pollutisoli, Corynebacterium imitans, Corynebacterium testudinoris*, or *Corynebacterium flavescens*. Specifically, the microorganism of the present disclosure may be *Corynebacterium stationis*, but is not limited thereto.

The term "purine nucleotide" herein refers to a nucleotide containing a purine-based structure. The purine nucleotide may be XMP, IMP, GMP, or AMP, and specifically IMP, XMP, or GMP. More specifically, the purine nucleotide may be XMP or GMP, but is not limited thereto.

The "inosine 5'-monophosphate or 5'-inosinic acid (IMP)" and "guanosine-5'-monophosphate or 5'-guanylic acid (GMP)" of the present disclosure, which are intermediates in the nucleic acid biosynthesis metabolic systems, have a physiologically important role in the body and are widely used in foods, pharmaceuticals, and the like. Specifically, IMP itself is known to impart a beef flavor, and GMP, derived from XMP, is known to impart a mushroom flavor. Both of the materials are known to enhance the flavor of monosodium glutamate (MSG), and thus have attracted much attention as a flavor-enhancing nucleic acid-based seasoning.

In an embodiment, GMP may be produced by conversion from XMP, but is not limited thereto. For example, the amount of GMP production can be increased by the conversion of the increasingly produced XMP to GMP, and thus the GMP is also included within the scope of the present disclosure.

The "XMP" of the present disclosure is also called xanthosine-5'-monophosphate or 5'-xanthylic acid, and may be formed from IMP through the action of IMP dehydrogenase or converted to GMP through the action of GMP synthase.

As used herein, the term "microorganism producing a purine nucleotide" encompasses all of wild-type microorganisms or naturally or artificially genetically modified microorganisms, and refers to a microorganism in which a particular mechanism is diminished or enhanced due to the insertion of an exogenous gene or the enhancement or inactivation of activity of an endogenous gene, wherein the microorganism may have a genetic mutation or enhanced activity for the production of a target purine nucleotide.

The microorganism of the present invention producing a purine nucleotide can retain enhanced ability to produce a target purine nucleotide by containing the glutamine-hydrolyzing GMP synthase variant of the present disclosure.

In an embodiment, the microorganism producing a purine nucleotide or the microorganism having purine nucleotide-producing ability in the present disclosure may be a microorganism in which some of the genes involved in the purine nucleotide biosynthesis are enhanced or diminished or some of the genes involved in the purine nucleotide degradation pathway are enhanced or diminished.

As used herein, the term "diminishment" of the activity of a polypeptide has a concept encompassing all of the reduction of activity or the absence of activity compared with the intrinsic activity. The diminishment may be used interchangeably with inactivation, deficiency, down-regulation, decrease, reduction, attenuation, or the like.

The diminishment may also include: a case where the activity of the polypeptide itself is reduced or eliminated compared with the activity of the polypeptide possessed by the original microorganism due to the mutation or the like of the polynucleotide encoding the polypeptide; a case where the activity and/or concentration (expression level) of the overall polypeptides in the cell is lower compared with the native strain due to the inhibition of the expression of a gene of a polynucleotide encoding the polypeptide or the inhibition of the translation into the polypeptide encoding the polynucleotide or the inhibition of translation into the polypeptide; a case where the expression of the polynucleotide is not made; and/or a case where the polypeptide has no activity in spite of the expression of the polynucleotide. The "intrinsic activity" refers to the activity of a specific polypeptide originally possessed by a parental strain before modification or a wild-type or non-modified microorganism, when the strain or microorganism is transformed by genetic mutation caused by natural or artificial factors. This term may be used interchangeably with the "activity before modification". The "inactivation, deficiency, decrease, down-regulation, reduction, or attenuation" of the activity of a polypeptide compared with the intrinsic activity thereof means that the activity of the polypeptide is lowered compared with the activity of a specific polypeptide originally possessed by a parent strain before transformation or a non-modified microorganism.

The diminishment of the activity of the polypeptide may be performing by any method known in the art, but is not limited thereto, and may be attained by applying various methods well known in the art (e.g., Nakashima N. et al., Bacterial cellular engineering by genome editing and gene silencing. *Int J Mol Sci.* 2014; 15(2):2773-2793, and Sambrook et al. *Molecular Cloning* 2012, etc.).

Specifically, the diminishment of the polypeptide of the present disclosure may be attained by:

1) deletion of a part or the entirety of the gene encoding the polypeptide;
2) modification of an expression control region (or expression control sequence) to reduce the expression of a gene encoding the polypeptide;
3) modification of the amino acid sequence constituting the polypeptide to eliminate or diminish the activity of the polypeptide (e.g., deletion/substitution/addition of at least one amino acid in the amino acid sequence);
4) modification of the gene sequence encoding the polynucleotide to eliminate or diminish the activity of the polypeptide (e.g., deletion/substitution/addition of at least one nucleotide in the nucleotide sequence of the polypeptide gene to encode the polypeptide modified to eliminate or diminish the activity of the polypeptide);
5) modification of a nucleotide sequence encoding an initiation codon or 5'-UTR region of the gene transcript encoding the polypeptide;
6) introduction of an antisense oligonucleotide (e.g., antisense RNA) complementarily binding to the gene transcript encoding the polypeptide;
7) addition of a sequence complementary to the Shine-Dalgarno sequence of the gene encoding the polypeptide to the upstream of the Shine-Dalgarno sequence to form a secondary structure that makes the attachment of ribosomes impossible;
8) addition of a promoter, which is to be reverse-transcribed, to the 3' end of the open reading frame (ORF) of the gene sequence encoding the polypeptide (reverse transcription engineering, RTE); or
9) combination of two or more selected from items 1) to 8), but is not particularly limited thereto.

For example, these are described as follows.

The deletion of a part or the entirety of the gene encoding the polypeptide in item 1) may be the elimination of the entirety of the polynucleotide encoding an endogenous target protein in the chromosome, the replacement with a polynucleotide with deletion of some nucleotides, or the replacement with a marker gene.

The modification of an expression control region (or expression control sequence) in item 2) may be the mutation on the expression control region (or expression control sequence) through deletion, insertion, non-conservative or conservative substitution, or a combination thereof, or the replacement with a sequence having more diminished activity. The expression control region includes a promoter, an operator sequence, a sequence for encoding a ribosomal binding site, and a sequence for controlling the termination of transcription and translation, but is not limited thereto.

The modification of the amino acid sequence or the polynucleotide sequence in items 3) and 4) may be the modification on the sequence through deletion, insertion, non-conservative or conservative substitution, or a combination thereof in the amino acid sequence of the polypeptide or the polynucleotide sequence encoding the polypeptide, or a replacement with an amino acid sequence or polynucleotide sequence modified to have more diminished activity or an amino acid sequence or polynucleotide sequence improved to have no activity, so as to diminish activity of the polypeptide. For example, the expression of the gene may be inhibited or attenuated by introducing mutation into the polynucleotide sequence to form a termination codon.

The modification of a nucleotide sequence encoding an initiation codon or 5'-UTR region of the gene transcript encoding the polypeptide in item 5) may be, for example, the substitution with a nucleotide sequence encoding, rather than an endogenous initiation codon, another initiation codon having a lower expression rate of the polypeptide, but is not limited thereto.

The introduction of an antisense oligonucleotide (e.g., antisense RNA) complementarily binding to the gene transcript encoding the polypeptide in item 6) may be referred to, for example, the literature (Weintraub, H. et al., Antisense-RNA as a molecular tool for genetic analysis, *Reviews—Trends in Genetics*, Vol. 1(1) 1986].

The addition of a sequence complementary to the Shine-Dalgarno sequence of the gene encoding the polypeptide to the upstream of the Shine-Dalgarno sequence so as to form a secondary structure that makes the attachment of ribosomes impossible in item 7) may be making mRNA translation impossible or reducing the rate thereof.

The addition of a promoter, which is to be reverse-transcribed, to the 3' end of the open reading frame (ORF) of the gene sequence encoding the polypeptide (reverse transcription engineering, RTE) in item 8) may be making an antisense nucleotide complementary to the gene transcript encoding the polypeptide to thereby diminish the activity of the polypeptide.

As used herein, the term "enhancement" in activity of a polypeptide refers to an increase in activity of the polypeptide compared with the intrinsic activity thereof. The enhancement may be used interchangeably with activation, up-regulation, overexpression, increase, or the like. Herein, the activation, enhancement, up-regulation, overexpression, and increase may include all of exhibiting the activity that has not been originally possessed or exhibiting the activity enhanced compared with the intrinsic activity or activity before modification. The "intrinsic activity" refers to the activity of a specific polypeptide originally possessed by a parental strain before transformation thereof or a non-modified microorganism when the strain or microorganism is transformed by genetic mutation caused by natural or artificial factors. This term may be used interchangeably with the "activity before modification". The "enhancement", "up-regulation", "overexpression", or "increase" in activity of a polypeptide compared with the intrinsic activity thereof means an improvement in activity and/or concentration (expression level) of a specific polypeptide originally possessed by a parent strain before transformation or a non-modified microorganism.

The enhancement can be attained through the introduction of an exogenous polypeptide or the activity enhancement and/or concentration (expression level) of an endogenous polypeptide. The enhancement of the activity of the polypeptide can be identified by an increase in activity degree or expression level of the corresponding polypeptide or amount of a product produced from the corresponding polypeptide.

The enhancement of the activity of the polypeptide may be attained by applying various methods well known in the art, and is not limited as long as the method can enhance the activity of the target polypeptide compared with the pre-transformation microorganism. Specifically, genetic engineering and/or protein engineering well known to a person skilled in the art, which is a routine method of molecular biology, may be used, but is not limited thereto (e.g., Sitnicka et al. Functional Analysis of Genes. *Advances in Cell Biology.* 2010, Vol. 2. 1-16, Sambrook et al. *Molecular Cloning* 2012, or the like).

Specifically, the enhancement of the polypeptide of the present disclosure may be attained by:

1) increase in intracellular copy number of the polynucleotide encoding the polypeptide;
2) replacement of a gene expression control region on the chromosome encoding the polypeptide with a sequence having higher activity;
3) modification of a nucleotide sequence encoding an initiation codon or 5'-UTR region of the gene transcript encoding the polypeptide;
4) modification of the amino acid sequence of the polypeptide to enhance activity of the polypeptide;
5) modification of the polynucleotide sequence encoding the polypeptide to enhance the activity of the polypeptide (e.g., modification of the polynucleotide sequence of the polypeptide gene to encode a polypeptide modified to enhance activity of the polypeptide);
6) introduction of an exogenous polypeptide exhibiting activity of the polypeptide or an exogenous polypeptide encoding the same;
7) codon optimization of the polynucleotide encoding the polypeptide;
8) modification or chemical modification of an exposed site selected by analysis of a tertiary structure of the polypeptide; or
9) combination of two or more selected from items 1) to 8), but is not particularly limited thereto.

More specifically, the enhancement of the polypeptide is described as follows.

The increase in intracellular copy number of the polynucleotide encoding the polypeptide in item 1) may be attained by the introduction, into a host cell, of a vector to which the polynucleotide encoding the corresponding polypeptide is operatively linked and which can replicate and function independently of the host. Alternatively, the increase in item 1) may be attained by the introduction of one or more copies of the polynucleotide encoding the corresponding polypeptide into the chromosome in a host cell. The introduction into the chromosome may be performed by the introduction, into a host cell, of a vector capable of inserting the polynucleotide into the chromosome in the host cell. The polynucleotide is as described above.

The replacement of a gene expression control region on the chromosome encoding the polypeptide with a sequence with strong activity in item 2) may be, for example, the modification on the sequence through deletion, insertion, non-conservative or conservative substitution, or a combination thereof, or the replacement with a sequence having stronger activity, to further enhance the activity of the expression control region. The expression control region may include, but not particularly limited to, a promoter, an operator sequence, a sequence encoding a ribosome binding site, a sequence controlling the termination of transcription and translation, and the like. For example, it may be the replacement of the original promoter with a stronger promoter, but is not limited thereto.

Examples of the known stronger promoter may be CJ1 to CJ7 promoters (U.S. Pat. No. 7,662,943 B2), lac promoter, trp promoter, trc promoter, tac promoter, lamda phage PR promoter, PL promoter, tet promoter, gapA promoter, SPL7 promoter, SPL13 (sm3) promoter (U.S. Ser. No. 10/584,338 B2), O2 promoter (U.S. Ser. No. 10/273,491 B2), tkt promoter, yccA promoter, and the like, but are not limited thereto.

The modification of a nucleotide sequence encoding an initiation codon or 5'-UTR region of the gene transcript encoding the polypeptide in item 3) may be, for example, the substitution with a nucleotide sequence encoding, rather than an endogenous initiation codon, another initiation codon having a higher expression rate of a polypeptide, but is not limited thereto.

The modification of the amino acid sequence or the polynucleotide sequence in items 4) and 5) may be the modification on the sequence through deletion, insertion, non-conservative or conservative substitution, or a combination thereof in the amino acid sequence of the polypeptide or the polynucleotide sequence encoding the polypeptide, or the replacement with an amino acid sequence or polynucleotide sequence modified to have stronger activity or an amino acid sequence or polynucleotide sequence modified to have increased activity, to enhance activity of the polypeptide. Specifically, the replacement may be performed by inserting the polynucleotide into the chromosome by homologous recombination, but is not limited thereto. The vector used herein may further include a selection maker for checking the insertion of the chromosome. The selection marker is as described above.

The introduction of an exogenous polypeptide exhibiting activity of the polypeptide in item 6) may be the introduction, into a host cell, of an exogenous polynucleotide encoding a polypeptide exhibiting the same/similar activity with regard to the polypeptide. The exogenous polynucleotide is not limited to the origin or sequence thereof as long as the exogenous polynucleotide exhibits the same/similar activity with regard to the polynucleotide. The introduction may be performed by any known transformation method appropriately selected by a person skilled in the art, and through the expression of the introduced polynucleotide in the host cell, the polypeptide is produced and the activity thereof can be enhanced.

The codon optimization of the polynucleotide encoding the polypeptide in item 7) may be the codon optimization of an endogenous polynucleotide to increase transcription or translation thereof in a host cell, or the codon optimization of an exogenous polynucleotide to allow optimized transcription or translation thereof in a host cell.

The modification or chemical modification of an exposed site selected by analysis of a tertiary structure of the polypeptide in item 8) may be, for example, the modification or chemical modification of an exposed site to be modified or chemically modified by comparing sequence information of a polypeptide to be analyzed with a database that stores sequence information of existing proteins, determining a template protein candidate according to similarity of the sequences, and identifying the structure based thereon.

Such enhancement of the activity of the polypeptide may mean that the activity, concentration, or expression level of the corresponding polypeptide is increased relative to the activity or concentration of the polypeptide expressed in a wild type or a microbial strain before modification, or that the amount of a product produced from the corresponding polypeptide is increased, but is not limited thereto.

The modification of a part or the entirety of the polynucleotide in the microorganism of the present disclosure may be induced by: (a) genome editing adopting homologous recombination or engineered nuclease (e.g., CRISPR-Cas9) using a vector for chromosomal insertion in a microorganism or and/or (b) the treatment with light, such as ultraviolet light and radiation, and/or chemicals, but is not limited thereto. The method of modifying a part or the entirety of the gene may include a method by DNA recombinant technology. For example, a nucleotide sequence or vector containing a nucleotide sequence homologous to a target gene may be introduced into the microorganism to bring about homologous recombination, resulting in deletion in a part or the entirety of the gene. The nucleotide sequence or vector to be introduced may include a dominant selection marker, but is not limited thereto.

Still another aspect of the present disclosure provides a method for producing a purine nucleotide, the method including culturing a microorganism including the variant of the present disclosure or a polynucleotide encoding the same.

The purine nucleotide production method of the present disclosure may include culturing, in a medium, a microorganism including the variant of the present disclosure, a polynucleotide encoding the same, or a vector including the polynucleotide.

As used herein the term "culture" refers to growing the microorganism of the present disclosure in appropriately adjusted environment conditions. The culture procedure of the present disclosure may be performed according to appropriate media or culture conditions known in the art. Such culture may be easily adjusted according to the selected strain by a person skilled in the art. Specifically, the culture may be in a batch type, a continuous type, and/or a fed-batch type, but is not limited thereto.

As used herein, the "medium" refers to a mixture containing, as main ingredients, nutrient materials required for culturing the microorganism, wherein the medium supplies nutrient materials, growth factors, and the like, including water that is essential for survival and growth. Specifically, as for the media and other culture conditions used for culturing the microorganism of the present disclosure, any medium that is used for usual culture of microorganisms may be used without particular limitation. However, the microorganisms of the present disclosure may be cultured under aerobic conditions in a conventional medium containing appropriate carbon sources, nitrogen sources, phosphorus sources, inorganic compounds, amino acids, and/or vitamins, while the temperature, pH, and the like are adjusted.

Specifically, a culture medium for the genus *Corynebacterium* strain may be found in the literature ("Manual of Methods for General Bacteriology" by the American Society for Bacteriology (Washington D.C., USA, 1981)).

In the present disclosure, the carbon source may include carbohydrates, such as glucose, saccharose, lactose, fructose, sucrose, and maltose; sugar alcohols, such as mannitol and sorbitol; organic acids, such as pyruvic acid, lactic acid, and citric acid; and amino acids, such as glutamic acid, methionine, and lysine. In addition, natural organic nutrient sources may be used, such as starch hydrolysates, molasses, blackstrap molasses, rice bran, cassava, bagasse, and corn steep liquor, and specifically, carbohydrates, such as glucose and sterile pretreated molasses (i.e., molasses converted to reduced sugars) may be used, and appropriate amounts of other carbon sources may be used without limitation. These carbon sources may be used alone or in a combination of two or more, but is not limited thereto.

As for the nitrogen sources, inorganic nitrogen sources, such as ammonia, ammonium sulfate, ammonium chloride, ammonium acetate, ammonium phosphate, ammonium carbonate, and ammonium nitrate; amino acids, such as glutamic acid, methionine, and glutamine; and organic nitrogen sources, such as peptone, NZ-amine, meat extracts, yeast extracts, malt extracts, corn steep liquor, casein hydrolysates, fishes or their decomposition products, defatted soybean cake or its degradation products, and the like may be used. These nitrogen sources may be used alone or in a combination of two or more thereof, but are not limited thereto.

Examples of the phosphate sources may include potassium phosphate monobasic, potassium phosphate dibasic, and sodium-containing salts corresponding thereto. As for inorganic compounds, sodium chloride, calcium chloride, iron chloride, magnesium sulfate, iron sulfate, manganese sulfate, calcium carbonate, and the like may be used, and besides, amino acids, vitamins, and/or suitable precursors may be included. These constituent ingredients or precursors may be added to the medium in a batch or continuous manner. However, the present disclosure is not limited thereto.

The pH of the medium may be adjusted by adding compounds, such as ammonium hydroxide, potassium hydroxide, ammonia, phosphoric acid, and sulfuric acid, to the medium in an appropriate manner during the culture of the microorganism of the present disclosure. In addition, an anti-foaming agent, such as a fatty acid polyglycol ester, may be added to suppress foam formation during the culture. In addition, oxygen or oxygen-containing gas may be injected into the medium to maintain the aerobic state of the medium, or nitrogen, hydrogen or carbon dioxide gas may be injected, or no gas may be injected, to maintain the anaerobic or non-aerobic state of the medium, but is not limited thereto.

In the culture of the present disclosure, the culture temperature may be maintained at 20° ° C. to 45° C., specifically 25° C. to 40° C., and the culture may be performed for about 10 hours to 160 hours, but is not limited thereto.

The purine nucleotide produced by the culture of the present disclosure may be released into the medium or may remain in cells without being released.

The purine nucleotide production method of the present disclosure may further include preparing the microorganism of the present disclosure, preparing a medium for culturing the microorganism, or a combination of these steps (regardless of the order, in any order), for example, before or after the culturing step.

The purine nucleotide production method of the present disclosure may further include recovering the purine nucleotide from a medium resulting from the culture (a medium in which culture has been performed) or the microorganism. The recovering step may be further included after the culturing step.

The recovering may be collecting a desired purine nucleotide by using an appropriate method known in the art according to the method for culturing a microorganism of the present disclosure, for example, a batch, continuous, or fed-batch type culture. For example, centrifugation, filtration, treatment with a crystallized protein precipitating agent (salting-out), extraction, ultrasonic disruption, ultrafiltration, dialysis, various types of chromatography, such as molecular sieve chromatography (gel filtration), adsorption chromatography, ion exchange chromatography, and affinity chromatography, HPLC, and a combination of these methods may be used, and a desired purine nucleotide may be recovered from the medium or microorganism by using an appropriate method known in the art.

The purine nucleotide production method of the present disclosure may further include a purification step. The purification may be performed by using an appropriate method known in the art. In an exemplary embodiment, when the purine nucleotide production method of the present disclosure includes both the recovering step and the purification step, the recovering step and the purification step may be performed continuously or discontinuously regardless of the order, or may be performed simultaneously or integrated into one step, but is not limited thereto.

In an exemplary embodiment, the GMP production method of the present disclosure may further include converting XMP into GMP. In the GMP production method of the present disclosure, the converting step may be further included after the culturing step or the covering step. The converting step may be performed by using an appropriate method known in the art. For example, the conversion may be performed using Coryneform bacteria, *E. coli*, or 5'-xanthylic acid aminase (KR 10-0655902 B1, US 2013-0095529 A1, or the like), but is not limited thereto.

In the method of the present disclosure, the variant, polynucleotide, vector, strain, purine nucleotide, and the like are as described in the other aspects above.

Still another aspect of the present disclosure is to provide a composition for producing a purine nucleotide, the composition containing the variant of the present disclosure, the polynucleotide encoding the variant, a microorganism including a vector including the polynucleotide or the polynucleotide of the present disclosure; a medium obtained by culturing the microorganism; or a composition thereof.

The composition of the present disclosure may further contain any appropriate excipient that is usually used in the composition for producing a purine nucleotide, and examples of the excipient may include a preserving agent, a wetting agent, a dispersing agent, a suspending agent, a buffer, a stabilizing agent, or an isotonic agent, but are not limited thereto.

In the composition of the present disclosure, the variant, polynucleotide, vector, microorganism, medium, purine nucleotide, and the like are as described in the other aspects above.

Still another aspect of the present disclosure is to provide a method for increasing purine nucleotide-producing ability of a microorganism, the method including modifying the microorganism to express the variant of the present disclosure.

In the method of the present application, the variant, polynucleotide, vector, microorganism, medium, purine nucleotide, and the like are as described in the other aspects above.

Still another aspect of the present disclosure provides use of the variant of the present disclosure for producing a purine nucleotide.

Still another aspect of the present disclosure provides use of the variant of the present disclosure, the polynucleotide encoding the same, or the microorganism including the vector including the same.

The variant, polynucleotide, vector, microorganism, and the like are as described in the other aspects above.

MODE FOR CARRYING OUT THE INVENTION

Hereinafter, the present disclosure will be described in detail with reference with examples and test examples. However, these examples and test examples are given for specifically illustrating the present disclosure, and the scope of the present disclosure is not limited thereto.

Example 1: Preparation of guaA Synthase-Diminished Variant

To discover a guaA variant for XMP production, a guaA mutant library, a gene encoding the variant, was constructed.

Example 1-1: Preparation of Vector Containing guaA

To prepare a guaA mutant library, a recombinant vector containing guaA was first constructed. PCR was performed using the chromosome of *Corynebacterium stationis* ATCC6872 as a template along with the primers of SEQ ID NO: 5 and SEQ ID NO: 6, and the amplification product was cloned into pCR2.1 vector by using a TOPO Cloning Kit (Invitrogen), and the resultant vector was named pCR-guaA.

TABLE 1

| SEQ ID NO | Primer name | Sequence (5'-3') |
|---|---|---|
| 5 | pCR-guaA-F | GCGATGTGATTGCCGGTG |
| 6 | pCR-guaA-R | GCTCTAGGAAGTCAGCAG |

Example 1-2: Construction of guaA Mutant Library

A guaA mutant library was constructed using as a template the pCR-guaA vector constructed in Example 1-1. The library was prepared by using an error-prone PCR kit (Clontech Diversify® PCR Random Mutagenesis Kit), and guaA mutant PCR products with different sequences were obtained by random mutagenesis using the primers of SEQ ID NOS: 7 and 8 according to the manual of a manufacturer. The amplification products were cloned using TOPO Cloning Kit (Invitrogen), and then transformed into *E. coli* DH5a and spread on an LB solid medium containing kanamycin (25 mg/L). The transformed *E. coli* colonies were collected to extract plasmids, which were named pCR-guaA-library.

TABLE 2

| SEQ ID NO | Primer name | Sequence (5'-3') |
|---|---|---|
| 7 | pCR-guaA-library-F | TGCCCAATACGCACAGCTG |
| 8 | pCR-guaA-library-R | GGCTGGGGCTTTGTCC |

Example 1-3: Evaluation of Constructed Library and Selection of Strain

The pCR-guaA-library prepared in Example 1-2 was transformed into the *Corynebacterium stationis* ATCC6872 wild-type strain by electroporation, and then the strain was spread on a nutrient medium containing 25 mg/L kanamycin to obtain 5,000 strain colonies into which the mutant gene was inserted. The respective colonies were named C.st ATCC6872_pCR_guaA(mt)1 to C.st ATCC6872_pCR_guaA(mt)5000.

Nutrient medium: 1% peptone, 1% beef extract, 0.25% sodium chloride, 1% yeast extract, 150 mg/L adenine, 150 mg/L guanine, 2% agar, pH 7.2 (based on 1 L of distilled water).

Each of the obtained 5,000 colonies was autoclaved under pressure, inoculated in 100 μL of a seed medium containing kanamycin (25 mg/L), cultured in a 96-deep-well plate with shaking at 30° C., 1200 rpm for 24 hours using a microplate shaker (TAITEC), and then used as a seed culture. The autoclaved fermentation medium of 320 μL (240 μL of a main medium+80 μL of a separate sterilized medium) was dispensed into a 96-deep well plate, and then each 15 μL of the seed culture was inoculated thereto, followed by culture with shaking under the same conditions as above for 72 hours.

To analyze the amount of XMP produced in the culture, 640 μL of sterile water was dispensed into the culture after the completion of culture, followed by centrifugation at 4000 rpm for 15 minutes, and then 3 μL of the supernatant was transferred to a 96-well UV plate into which 297 μL of distilled water was dispensed. Next, a microplate reader was used to perform shaking for 30 seconds, and a spectrophotometer was used to measure the absorbance at 25° C. and a wavelength of 260 nm. Then, ten colonies of mutant strains showing an increase in absorbance compared with the wild-type strain were selected. Other colonies showed similar or decreased degrees of absorbance compared with the control.

The ten selected strains were repeatedly measured for absorbance by way of the above method and investigated for the amount of XMP production, and one species of strain (C.st ATCC6872_pCR_guaA(mt)726) having significantly enhanced XMP-producing ability compared with the wild-type strain was selected.

To verify the validity of the finally selected strain, a fermentation titer test was performed.

The *Corynebacterium stationis* ATCC6872 wild-type strain and the selected C.st ATCC6872_pCR_guaA(mt)726 strain were inoculated in 14 mL tubes containing 2.5 mL of the seed medium below and cultured with shaking at 170 rpm for 24 hours at 30° C. In a 250 mL corner-baffle flask containing 32 mL of the following production medium (24 mL of a main medium+8 mL of a separate sterile medium), 0.7 mL of the seed culture was inoculated and cultured with shaking at 170 rpm for 75 hours at 30° C.

The compositions of the seed medium, main medium, and separate sterile medium are as follows.

<XMP Flask Seed Medium>

30 g/L glucose, 15 g/L peptone, 15 g/L of yeast extract, 2.5 g/L sodium chloride, 3 g/L urea, 150 mg/L adenine, 150 mg/L guanine, pH 7.0 (on the basis of 1 L of distilled water).

<XMP Flask Production Medium (Main Medium)>

50 g/L glucose, 10 g/L magnesium sulfate, 3 g/L yeast extract, 100 mg/L calcium chloride, 20 mg/L iron sulfate, 10 mg/L manganese sulfate, 10 mg/L zinc sulfate, 0.8 mg/L copper sulfate, 20 mg/L histidine, 15 mg/L cystine, 15 mg/L beta-alanine, 100 μg/L biotin, 5 mg/L thiamine, 50 mg/L adenine, 25 mg/L guanine, 15 mg/L niacin, pH 7.0 (on the basis of 1 L of distilled water).

<XMP Flask Production Medium (Separate Sterile Medium)>

18 g/L potassium phosphate monobasic, 42 g/L potassium phosphate dibasic, 7 g/L urea, 5 g/L ammonium sulfate (on the based on 1 L of distilled water)

The results of measuring the amount of XMP production by a method using HPLC after completion of culture are shown in Table 3.

TABLE 3

| Strain | XMP concentration (g/L) |
|---|---|
| C.st ATCC6872 | 0 |
| C.st ATCC6872_pCR_guaA(mt)726 | 4.83 |

As shown in Table 3, the concentration of XMP produced was 4.83 g/L in C.st ATCC6872_pCR_guaA(mt)726 compared with the wild-type strain.

Example 1-4: Identification of Mutation Through Gene Sequencing

To identify the sequence of the guaA variant of the C.st ATCC6872_pCR_guaA(mt)726 strain, the C.st ATCC6872_pCR_guaA(mt)726 strain was subjected to PCR using the primers of SEQ ID NOS: 8 and 9 and sequencing. As a result of comparison with the sequence of the guaA gene of the wild-type strain, the C.st ATCC6872_PCR_guaA(mt)726 strain was identified to include a mutation in which the amino acid at position 29 in the guaA gene is substituted from arginine to cysteine (the nucleotide at position 85 being substituted from c to t: SEQ ID NO: 2).

The identified variant sequence is shown in Table 4.

TABLE 4

| SEQ ID NO | Variant Sequence |
|---|---|
| 1 | **M**TQPATTPRPVLVVDFGAQYAQLIARRVCEASIYSEVVPHSATV KEIKAKNPAALILSGGPSSVYADGAPQLKPELLELGVPVFGICYG FQAMNHALGGNVAQTGDREYGRTEITHTGGVLHDGLEENHKV WMSHGDAVDKAPEGFTVTASSAGAPVAAMECVAKQMAGVQY HPEVMHSPHGQEVLVRFLTEVAGLEQTWTSANIAQQLIDDVRA QIGPEGRAICGLSGGVDSAVAAALVQRAIGDRLTCVFVDHGLLR AGEREQVEKDFVASTGAKLITAHEADAFLSKLAGVTDPEAKRK AIGAEFIRSFERAVAQALEESPEDSTVDFLVQGTLYPDVVESGG GDGTANIKSHHNVGGLPDDVEFELVEPLRLLFKDEVRAVGREL GLPEEIVARQPFPGPGLGIRIIGEVTEERLEILRQADLIARTELTN AGLDGDIWQCPVVLLADVRSVGVQGDGRTYGHPIVLRPVSSE DAMTADWTRVPYDVLEKISTRITNEVNDVNRVVVDITSKPPGTI EWE |

In the following examples, it was investigated whether the guaA mutation had an effect on XMP production.

Example 2: Identification of Effect of guaA Variant

Example 2-1: Construction of Vector for guaA Variant Expression

To investigate the effect, on XMP production, of the variant (R29C; SEQ ID NO: 1) in which arginine at position 29 in the guaA enzyme amino acid sequence was substituted with cysteine, a vector for preparing an expression strain thereof was constructed as follows by using the plasmid pDCM2 (Korea Publication No. 10-2020-0136813) for gene insertion and replacement in the *Corynebacterium* chromosome.

PCR was performed by using the chromosome of *Corynebacterium stationis* ATCC6872 as a template along with the primer pairs of SEQ ID NOS: 10 and 11 and SEQ ID NOS: 12 and 13. Solg™ Pfu-X DNA polymerase was used as the polymerase, and PCR was performed under PCR amplification conditions: denaturation at 95° C. for 5 minutes, 30 cycles of denaturation at 95° C. for 30 seconds, annealing at 58° C. for 30 seconds, and polymerization at 72° C. for 60 seconds, and then a polymerization reaction at 72° C. for 5 minutes to thereby obtain each PCR product. The amplification product was mixed with the pDCM2 vector previously prepared by digestion with SmaI restriction enzyme, and cloned by the Gibson assembly (DG Gibson et al., *NATURE METHODS*, Vol. 6 No. 5, May 2009, NEBuilder HiFi DNA Assembly Master Mix) method to obtain a recombinant plasmid, which was named pDCM2-guaA (R29C). The cloning was performed by mixing the Gibson assembly reagent and each of the gene fragments in a calculated number of moles, followed by preservation at 50° C. for 1 hour.

Example 2-2: Preparation of guaA Variant-Expressing Strain

The pDCM2-guaA(R29C) vector constructed in the above example was transformed into the *Corynebacterium stationis* ATCC6872 strain by electroporation, and strains having the vector inserted into the chromosome by recombination of homologous sequences were selected on a medium containing 25 mg/L kanamycin. The selected primary strains were subjected to secondary cross-over to select a strain having mutation introduced into the target gene. The introduction of gene mutation in the finally transformed strain was investigated by PCR using the primer pair of SEQ ID NO: 14 and SEQ ID NO: 15 and sequencing, and the confirmed strain was named C.st ATCC6872::guaA (R29C).

Example 2-3: Comparison of XMP-Producing Ability of guaA Variant-Expressing Strain The XMP-producing abilities of the C.st ATCC6872::guaA(R29C) strain prepared in Example 2-2 and the wild-type strain were investigated through the fermentation titer evaluation method in Example 1-3. After completion of culture, the amount of XMP production was measured by HPLC, and the culture results are shown in Table 5.

The test was repeated three times, and the mean values of the analysis results are shown in Table 5.

TABLE 5

| Strain | XMP concentration (g/L) |
|---|---|
| C.st ATCC6872 | 0 |
| C.st ATCC6872::guaA(R29C) | 5.21 |

As shown in Table 5, the concentration of XMP produced was 5.21 g/L in the C.st ATCC6872::guaA(R29C) strain.

The C.st ATCC6872::guaA(R29C) strain was named CN02-2299, which was deposited with the Korea Microorganism Conservation Center, a depository institution under the Budapest Treaty, on 9 Aug. 2021, and given accession number KCCM13029P.

Example 3: Substitution of Amino Acid with Other Amino Acids in guaA Mutation

Example 3-1: Construction of Vector for Amino Acid Substitution and Insertion for guaA Mutation It was identified through the above example that XMP could be produced by guaA(R29C) mutation. To investigate the positional importance of guaA mutation, vectors for substitution of the amino acid at position 29 with other amino acids were constructed, and the effect on XMP-producing ability was investigated. Site-directed mutagenesis was performed by using the pDCM2-guaA(R29C) vector constructed in Example 2-1 as a template.

Specifically, PCR was performed using the primer pairs of SEQ ID NOS: 10 and 16 and SEQ ID NOS: 17 and 13, primer pairs of SEQ ID NOS: 10 and 18 and SEQ ID NOS: 19 and 13, primer pairs of SEQ ID NOS: 10 and 20 and SEQ ID NOS: 21 and 13, primer pairs of SEQ ID NOS: 10 and 22 and SEQ ID NOS: 23 and 13, primer pairs of SEQ ID NOS: 10 and 24 and SEQ ID NOS: 25 and 13, primer pairs of SEQ ID NOS: 10 and 26 and SEQ ID NOS: 27 and 13, primer pairs of SEQ ID NOS: 10 and 28 and SEQ ID NOS: 29 and 13, primer pairs of SEQ ID NOS: 10 and 30 and SEQ ID NOS: 31 and 13, primer pairs of SEQ ID NOS: 10 and 32 and SEQ ID NOS: 33 and 13, primer pairs of SEQ ID NOS: 10 and 34 and SEQ ID NOS: 35 and 13, primer pairs of SEQ ID NOS: 10 and 36 and SEQ ID NOS: 37 and 13, primer pairs of SEQ ID NOS: 10 and 38 and SEQ ID NOS: 39 and 13, primer pairs of SEQ ID NOS: 10 and 40 and SEQ ID NOS: 41 and 13, primer pairs of SEQ ID NOS: 10 and 42 and SEQ ID NOS: 43 and 13, primer pairs of SEQ ID NOS: 10 and 44 and SEQ ID NOS: 45 and 13, primer pairs of SEQ ID NOS: 10 and 46 and SEQ ID NOS: 47 and 13, primer pairs of SEQ ID NOS: 10 and 48 and SEQ ID NOS: 49 and 13, and primer pairs of SEQ ID NOS: 10 and 50 and SEQ ID NOS: 51 and 13. Solg™ Pfu-X DNA polymerase was used as the polymerase, and PCR was performed under PCR amplification conditions: with denaturation at 95° C. for 5 minutes, 30 cycles of denaturation at 95° C. for 30 seconds, annealing at 58° C. for 30 seconds, and polymerization at 72° C. for 60 seconds, and then a polymerization reaction at 72° C. for 5 minutes to thereby obtain each PCR product. The respective amplification products were mixed with the pDCM2 vector previously prepared by digestion with SmaI restriction enzyme, and cloned by the Gibson assembly method to obtain recombinant plasmids, and the plasmid information thus obtained is shown in Table 6. The cloning was performed by mixing the Gibson assembly reagent and the respective fragments in a calculated number of moles, followed by preservation at 50° C. for 1 hour.

TABLE 6

| NO | Plasmid Name |
|---|---|
| 1 | pDCM2-guaA(R29G) |
| 2 | pDCM2-guaA(R29F) |
| 3 | pDCM2-guaA(R29S) |
| 4 | pDCM2-guaA(R29Y) |
| 5 | pDCM2-guaA(R29W) |
| 6 | pDCM2-guaA(R29I) |
| 7 | pDCM2-guaA(R29V) |
| 8 | pDCM2-guaA(R29P) |
| 9 | pDCM2-guaA(R29T) |
| 10 | pDCM2-guaA(R29A) |
| 11 | pDCM2-guaA(R29D) |
| 12 | pDCM2-guaA(R29N) |
| 13 | pDCM2-guaA(R29H) |
| 14 | pDCM2-guaA(R29L) |
| 15 | pDCM2-guaA(R29M) |
| 16 | pDCM2-guaA(R29Q) |
| 17 | pDCM2-guaA(R29K) |
| 18 | pDCM2-guaA(R29E) |

Example 3-2: Preparation of Strains Having Substitutions of Mutation in guaA Variant with Other Amino Acids and Comparison of XMP-Producing Ability The 18 vectors for mutation introduction obtained in Example 3-1 were transformed into the *Corynebacterium stationis* ATCC6872 wild-type strain, and strains having the vectors inserted into the chromosome by recombination of homologous sequences were selected on a medium containing 25 mg/L kanamycin. The selected primary strains were subjected to secondary cross-over to select strains having mutation introduced into the target gene. The introduction of gene mutation in the finally transformed strains was investigated by PCR using the primer pair of SEQ ID NO: 14 and SEQ ID NO: 15 and sequencing, and the strain names according to the inserted mutations are shown in Table 7 below.

TABLE 7

| NO | Strain name |
|---|---|
| 1 | C.st ATCC6872::guaA(R29G) |
| 2 | C.st ATCC6872::guaA(R29F) |
| 3 | C.st ATCC6872::guaA(R29S) |
| 4 | C.st ATCC6872::guaA(R29Y) |
| 5 | C.st ATCC6872::guaA(R29W) |
| 6 | C.st ATCC6872::guaA(R29I) |
| 7 | C.st ATCC6872::guaA(R29V) |
| 8 | C.st ATCC6872::guaA(R29P) |
| 9 | C.st ATCC6872::guaA(R29T) |
| 10 | C.st ATCC6872::guaA(R29A) |
| 11 | C.st ATCC6872::guaA(R29D) |
| 12 | C.st ATCC6872::guaA(R29N) |
| 13 | C.st ATCC6872::guaA(R29H) |
| 14 | C.st ATCC6872::guaA(R29L) |
| 15 | C.st ATCC6872::guaA(R29M) |
| 16 | C.st ATCC6872::guaA(R29Q) |
| 17 | C.st ATCC6872::guaA(R29K) |
| 18 | C.st ATCC6872::guaA(R29E) |

The prepared strains, the C.st ATCC6872::guaA(R29C) strain, and the wild-type strain were cultured and analyzed for the XMP concentration by way of the fermentation titer evaluation method in Example 1-3. The test was repeated three times, and the mean values of the analysis results are shown in Table 8.

TABLE 8

| Strain | XMP concentration (g/L) |
|---|---|
| C.st ATCC6872 | 0 |
| C.st ATCC6872::guaA(R29C) | 5.01 |
| C.st ATCC6872::guaA(R29G) | 4.95 |
| C.st ATCC6872::guaA(R29F) | 4.33 |
| C.st ATCC6872::guaA(R29S) | 4.01 |
| C.st ATCC6872::guaA(R29Y) | 4.88 |
| C.st ATCC6872::guaA(R29W) | 2.24 |
| C.st ATCC6872::guaA(R29I) | 4.77 |
| C.st ATCC6872::guaA(R29V) | 4.89 |
| C.st ATCC6872::guaA(R29P) | 4.18 |
| C.st ATCC6872::guaA(R29T) | 4.77 |
| C.st ATCC6872::guaA(R29A) | 4.22 |
| C.st ATCC6872::guaA(R29D) | 4.16 |
| C.st ATCC6872::guaA(R29N) | 4.93 |
| C.st ATCC6872::guaA(R29H) | 0.25 |
| C.st ATCC6872::guaA(R29L) | 4.76 |
| C.st ATCC6872::guaA(R29M) | 4.24 |
| C.st ATCC6872::guaA(R29Q) | 4.88 |
| C.st ATCC6872::guaA(R29K) | 4.93 |
| C.st ATCC6872::guaA(R29E) | 4.99 |

Referring to Table 8, the strains including guaA in which the amino acid at position 29 in the amino acid sequence encoded by the guaA gene is substituted with other amino acids except for arginine were identified to produce XMP compared with the wild-type strain. That is, the amino acid at position 29 in the amino acid sequence encoded by guaA gene corresponded to a major mutation position in XMP production, and more specifically, when the amino acid at position 29 in the amino acid sequence encoded by the guaA gene was substituted with other amino acids except for arginine (cysteine, glycine, phenylalanine, serine, tyrosine, tryptophan, isoleucine, valine, proline, threonine, alanine, aspartic acid, asparagine, histidine, leucine, methionine, glutamine, lysine, and glutamic acid), the amounts of XMP produced by the microorganisms containing such mutation can be greatly increased.

It can be therefore seen that the variants having substitutions of the amino acid at position 29 in guaA with other amino acids can be advantageously used in the production of a purine nucleotide.

Example 4: Identification of GMP Producing Ability of guaA Variant-Expressing Strain The production of GMP was investigated using an XMP culture of C.st ATCC6872::guaA(R29C) as an XMP-producing strain by the following method (see Korean Patent No. KR 10-0655902 B1 and U.S. Patent Publication No. US 2013-0095529 A1).

The C.st ATCC6872::guaA(R29C) strain was cultured by the fermentation titer evaluation method in Example 1-3. After completion of culture, the amount of XMP production was measured by a method using HPLC. For a conversion reaction of the produced XMP to GMP, the following conversion reaction additives and *E. coli* XMP aminase were added to the fermentation liquid in the corner-baffle flask to perform a conversion reaction at 40° C. for 2.5 hours.

<Conversion Reaction Additives>

1.8 g/L phytic acid, 4.8 g/L magnesium sulfate, 3 mL/L nymeen, 2% xylene, 100 mg/L adenine, 7.7 g/L sodium phosphate dibasic ($Na_2HPO_4$), 2 g/L glutamine, 46 g/L glucose.

As a result of the test, the conversion rate indicating the amount of GMP production compared with the amount of XMP consumption is shown in Table 9.

TABLE 9

| Strain name | Concentration (g/L) XMP | Concentration (g/L) GMP | Conversion rate (%) (GMP production/ XMP consumption) |
|---|---|---|---|
| C.st ATCC6872::guaA(R29C) | 4.91 | 3.54 | 72.1 |

As shown in Table 9, 3.54 g/L GMP was produced through the conversion reaction from XMP produced by the C.st ATCC6872::guaA(R29C) strain.

It was therefore identified that the variant having a substitution of the amino acid at position 29 in guaA with another amino acid increased the GMP production, and thus it can be seen that the variant provided in the present disclosure can be advantageously used in the production of a purine nucleotide.

As set forth above, a person skilled in the art to which the present disclosure pertains will be able to understand that the present disclosure may be embodied in other specific forms without departing from the technical spirit or essential characteristics thereof. Therefore, the embodiments described above should be construed as being exemplified and not limiting the present disclosure. The scope of the present disclosure should be understood that all changes or modifications derived from the definitions and scopes of the claims and their equivalents fall within the scope of the disclosure.

The invention claimed is:

1. A glutamine-hydrolyzing guanosine-5'-monophosphate (GMP) synthase variant in which the amino acid corresponding to position 29 in SEQ ID NO: 3 is substituted with a different amino acid, wherein the variant has 90% or more of sequence identity with the amino acid sequence of SEQ ID NO: 3, and wherein the variant has glutamine-hydrolyzing GMP synthase activity.

2. The glutamine-hydrolyzing GMP synthase variant of claim 1, wherein the amino acid corresponding to position 29 in SEQ ID NO: 3 is substituted with an amino acid selected from glycine, alanine, valine, leucine, isoleucine, methionine, phenylalanine, tryptophan, praline, serine, threonine, cysteine, tyrosine, asparagine, glutamine, aspartic acid, glutamic acid, lysine, and histidine.

3. A microorganism, wherein the microorganism comprises the glutamine-hydrolyzing GMP synthase variant of claim 1, or wherein the microorganism comprises a polynucleotide encoding the variant.

4. A method for producing a purine nucleotide, the method comprising culturing the microorganism of claim 3 in a culture medium to thereby produce a purine nucleotide.

5. The method of claim 4, further comprising recovering the purine nucleotide from a culture medium or the microorganism.

6. A composition for producing a purine nucleotide, the composition comprising at least one of: the glutamine-hydrolyzing GMP synthase variant of claim 1; a microorganism comprising the variant; and a medium comprising the microorganism.

7. A method for increasing purine nucleotide-producing ability of a microorganism, the method comprising modifying the microorganism to express the variant of claim 1 and wherein the microorganism modified to express the variant of claim 1 has increased ability for purine nucleotide production relative to a microorganism not modified to express the variant of claim 1.

8. The microorganism of claim 3, wherein the microorganism is *Corynebacterium stationis.*

9. A method for producing a purine nucleotide, the method comprising culturing the microorganism of claim 8 in a culture medium to thereby produce a purine nucleotide.

10. The method of claim 9, further comprising recovering the purine nucleotide from a culture medium or the microorganism.

11. A polynucleotide comprising a nucleotide sequence encoding the variant of claim 1.

* * * * *